US012329570B2

United States Patent
Xie et al.

(10) Patent No.: US 12,329,570 B2
(45) Date of Patent: Jun. 17, 2025

(54) ULTRASOUND SYSTEM WITH AN ARTIFICIAL NEURAL NETWORK FOR GUIDED LIVER IMAGING

(71) Applicant: KONINKLIJKE PHILIPS N.V., Eindhoven (NL)

(72) Inventors: Hua Xie, Cambridge, MA (US); Christine Menking Swisher, San Diego, CA (US); Claudia Errico, Cambridge, MA (US); Vijay Thakur Shamdasani, Kenmore, WA (US); Yinhui Deng, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 718 days.

(21) Appl. No.: 17/263,172

(22) PCT Filed: Jul. 22, 2019

(86) PCT No.: PCT/EP2019/069637
§ 371 (c)(1),
(2) Date: Jan. 26, 2021

(87) PCT Pub. No.: WO2020/020809
PCT Pub. Date: Jan. 30, 2020

(65) Prior Publication Data
US 2021/0177373 A1 Jun. 17, 2021

Related U.S. Application Data

(60) Provisional application No. 62/711,974, filed on Jul. 30, 2018.

(30) Foreign Application Priority Data

Jul. 26, 2018 (WO) ................ PCT/CN2018/097194

(51) Int. Cl.
A61B 8/08 (2006.01)
A61B 8/00 (2006.01)
(Continued)

(52) U.S. Cl.
CPC ................ A61B 8/085 (2013.01); A61B 8/14 (2013.01); A61B 8/463 (2013.01); A61B 8/469 (2013.01);
(Continued)

(58) Field of Classification Search
CPC .......... A61B 8/085; A61B 8/14; A61B 8/463; A61B 8/469; G06N 3/04; G06N 3/08;
(Continued)

(56) References Cited

U.S. PATENT DOCUMENTS 6,443,896 B1    9/2002  Detner
6,530,885 B1 *  3/2003  Entrekin ............. G01S 7/52053
                                                        600/443

(Continued)

FOREIGN PATENT DOCUMENTS

JP        2011005026      *  1/2011  ............. G16H 50/70
WO   WO-2018037382 A1  *  3/2018  ............. A61K 31/05

OTHER PUBLICATIONS

Kim, K.B. et al., "Quantification of Hepatorenal Index for Computer-Aided Fatty Liver Classification with Self-Organizing Map and Fuzzy Stretching from Ultrasonography", BioMed Research International, 2015, vol. 2015, Article ID 535894, 9 pages.

(Continued)

Primary Examiner — Rochelle D Turchen

(57) ABSTRACT

The present disclosure describes ultrasound imaging systems and methods for ultrasonically inspecting biological tissue, such as liver and for automatically identifying and acquiring a view suitable for hepatic-renal echo-intensity ratio quantification, using one or more neural networks, (Continued)

which may be trained to perform image classification, segmentation, or a combination thereof to compute a confidence metric and to provide a recommendation for measurement ROIs placement on the image.

22 Claims, 14 Drawing Sheets

(51) Int. Cl.
| | |
|---|---|
| *A61B 8/14* | (2006.01) |
| *G06N 3/04* | (2023.01) |
| *G06N 3/08* | (2023.01) |
| *G06T 7/10* | (2017.01) |
| *G16H 30/40* | (2018.01) |
| *G16H 50/20* | (2018.01) |

(52) U.S. Cl.
CPC .................. *G06N 3/04* (2013.01); *G06N 3/08* (2013.01); *G06T 7/10* (2017.01); *G16H 30/40* (2018.01); *G16H 50/20* (2018.01); *G06T 2207/10132* (2013.01); *G06T 2207/20081* (2013.01); *G06T 2207/20084* (2013.01); *G06T 2207/30056* (2013.01); *G06T 2207/30084* (2013.01)

(58) Field of Classification Search
CPC ............. G06T 7/10; G06T 2207/10132; G06T 2207/20081; G06T 2207/20084; G06T 2207/30056; G06T 2207/30084; G16H 30/40; G16H 50/20

See application file for complete search history.

(56) References Cited

U.S. PATENT DOCUMENTS

| | | | |
|---|---|---|---|
| 2006/0120608 A1* | 6/2006 | Luo | ....................... G06T 7/0012 382/224 |
| 2010/0331700 A1 | 12/2010 | Baba et al. | |
| 2016/0155227 A1 | 6/2016 | Chae | |
| 2017/0360403 A1 | 12/2017 | Rothberg et al. | |
| 2018/0103912 A1 | 4/2018 | Canfield et al. | |

OTHER PUBLICATIONS

Santos, J. et al., "Detection of pathologic liver using ultrasound images", Biomedical Signal Processing and Control, 2014, vol. 14, pp. 248-255.
Andrade, A. et al., "Classifier Approaches for Liver Steatosis using Ultrasound Images", Procedia Technology, 2012, vol. 5, pp. 763-770.
American Liver Association: "Nonalcoholic Fatty Liver Disease"; Downloaded From www.liverfoundation.org.abouttheliver.info. nahld, 2017, 2 page document.
Debevec et al: "Recovering High Dynamic Range Radiance Maps From Photographs"; SIGGRAPH, 1997, 10 Page Document.
Fan: "Epidemiology of Alcoholic and Nonalcoholic Fatty Liver Disease in China"; Journal of Gastroenterology and Hepatology, 2013, 28(Suppl. 1), pp. 11-17.
Girshick et al "Fast R-CNN"; arXiv:1504.08083V2 [cs.CV]. Sep. 27 2015, 9 Page Document.
Long et al: "Fully Convolutional Networks for Semantic Segmentation"; arXiv:1411.4038v2 [cs.Cv], Mar. 8, 2015, 10 Page Document.
Mancini et al: Metabolism Clinical and Experimental, 58 (2009), pp. 1724-1730.
PCT/EP2019/069637 ISR & WO, Nov. 7, 2019, 16 Page Document.
Von Volkmann et al: "Quantitative Measurement of Ultrasound Attenuation and Hepato-Renal Index in Non-Alcoholic Fatty Liver Disease"; Med Ultrason 2013, vol. 15, No. 1, pp. 16-22, 7 Page Document.
Xia et al: "Standardization Ultrasound Hepatic/Renal Ration and Hepatic Attenuation Reate to Quantify Liver Fat Content: an Improvement Method"; Obesity/vol. 20, Issue 2, 33 Page Document.
Zhang et al: "Ultrasound Hepatic/Renal Ratio and Hepatic Attenuation Rate for Quantifying Liver Fat Content"; World Journal of Gastroenterology; 2014, vol. 20 (47), pp. 17985-17992.

* cited by examiner

ULTRASOUND SYSTEM WITH AN ARTIFICIAL NEURAL NETWORK FOR GUIDED LIVER IMAGING

CROSS-REFERENCE TO PRIOR APPLICATIONS

This application is the U.S. National Phase application under 35 U.S.C. § 371 of International Application No. PCT/EP2019/069637, filed on Jul. 22, 2019, which claims the benefit of Chinese Patent Application No. PCT/CN2018/097194, filed on Jul. 26, 2018, and U.S. Provisional Patent Application No. 62/711,974, filed Jul. 30, 2018. These applications are hereby incorporated by reference herein.

TECHNICAL FIELD

The present disclosure pertains to ultrasound imaging systems and methods for ultrasonically inspecting biological tissue, and more specifically for guided, and at least partially automated, hepatic-renal ratio quantification using an artificial neural network.

BACKGROUND

Ultrasound imaging is commonly used to non-invasively image internal tissue or organs of a patient, e.g., for diagnosing any number of different diseases and the progression or success of treatment thereof. For example, the ratio of echo-intensity between liver and kidney is a quantitative biomarker for liver fat content. Ultrasound imaging can be used to measure this ratio, but it may be subject to misdiagnoses or classification due to difficulties in achieving the proper frame for measurement purposes. While existing systems may provide tools that aim to improve the acquisition of image data, for example for hepatic renal ratio quantification, existing systems may have shortcomings, thus designers and manufacturers ultrasound imaging system continue to seek improvements thereto.

SUMMARY

The present disclosure describes systems and methods for ultrasound imaging, which in some examples may be well suited for automated hepatic renal ration quantification using an artificial neural network. In embodiments and as described further below, one or more artificial neural networks may be used, for example to guide the acquisition of an ultrasound image suitable for hepatic renal ratio quantification, as well as to provide additional guidance (e.g., for ROI placement) and for automating certain aspects of the process.

In accordance with some examples of the present disclosure, an ultrasound system may include a probe configured to transmit ultrasound toward a subject for generating a real-time (or live) image of biological tissue of the subject, and a processor which is configured to receive the real-time image and to output a confidence metric for the real-time image, the confidence metric being indicative of a probability of the real-time ultrasound image visualizing the biological tissue in accordance with a target image view. In at least some embodiments, the processor may employ at least one artificial neural network to generate the confidence metric. Upon determination that the confidence metric exceeds a threshold value, the processor may be further configured to automatically capture (i.e. store in local memory) the real-time ultrasound image, to determine locations of first and second regions of interest (ROIs), and to compute a ratio of the echo-intensity values of the first and second ROIs. The processor may be further configured, if the confidence metric does not exceed the threshold value, to automatically receive one or more successive real-time image frames and output a confidence metric for each of the one or more successive real-time image frames so as to continue the process of identifying a suitable image frame for echo-intensity ration quantification. In one embodiment, the system is specifically configured for ultrasonically inspecting liver tissue, thus the biological tissue in the image frames may include at least one of hepatic tissue, renal tissue, or a combination thereof, and wherein the neural network may be specifically trained to produce a confidence metric that exceeds the threshold value if the input image corresponds to a sagittal liver and right kidney view suitable for computing the hepatic-renal echo-intensity ratio.

In some embodiments, the artificial neural network may include a deep convolutional neural network trained to segment the input image to generate a segmentation map, and the confidence metric may be based, at least in part, on the segmentation map of the real-time image. In some examples, a processor (implementing e.g., another neural network or a non machine-learning algorithm) may compare the segmentation map output by the segmentation neural network to a segmentation map or image corresponding to the target image view. The comparison may be done by a neural network or other image processing technique, for example by overlaying the two maps and quantifying the differences. In yet other examples, the confidence metric may be computed by quantitatively analyzing the content of the segmentation map, e.g., to determine whether the map, and thus the source image, contains a sufficient amount of a particular type of tissue (e.g., kidney tissue) and/or the image visualizes the particular type of tissue in the appropriate location within the image. In some such embodiments, the neural network may include a fully convolutional network configured to propagate the input image along a contracting path followed by an expanding path to generate the segmentation map. In some examples, the fully convolutional network may include a symmetric network with a number of down-sampling convolutional layers along the contracting path and a same number of up-sampling convolutional layers along the expanding path.

In some embodiments, the confidence metric may be determined by classifying the input image into one of a plurality of categories. In such examples, the neural network may include a deep convolutional network configured to classify an input image into one of a plurality of categories or classes, each of which may be associated with one of a plurality of different confidence metric values. In such examples, upon classification of the image into a category, the system may proceed to segment the image (using a neural network or a non-machine learning based approach) to identify the regions within the image which correspond to different types of tissue and thus to automatically generate recommended ROIs for measuring the echo-intensity ratio. In some examples, the recommended ROIs are displayed with the image (e.g., overlaid at the respective locations in the image) and upon a selection by the user, the system sets the ROIs for measurement to the recommended ROIs and computes the echo-intensity ratio. In some embodiments, the system may be further configured to provide guidance to the user during acquisition of the suitable view, such as by displaying a graphical indicator that represents the current value of the confidence metric. The graphical indicator is dynamically updated in real-time while the system performs view identification or matching in the background such that at any given time, the graphical indicator represents the current computed value of the confidence metric.

A method of ultrasonically inspecting biological tissue in accordance with some examples may include receiving, by a processor of an ultrasound system, a real-time ultrasound image representative of one or more types of biological tissue, and providing the real-time ultrasound image to at least one convolutional neural network trained to output a confidence metric for each input image. As will be further described, the confidence metric may be indicative of a probability of the real-time ultrasound image visualizing the biological tissue in accordance with a target image view. The example method may continue, if the confidence metric is determined by the ultrasound system to exceed a threshold value, by automatically storing the real-time ultrasound image in local memory of the ultrasound system, determining locations of regions of interest (ROIs), and computing a ratio of an echo-intensity value of a first region of interest to that of a second regions of interest (ROIs). If the confidence metric is determined not to exceed the threshold value, the method may continue by automatically providing one or more successive real-time images to the at least one convolutional neural network for determining a confidence metric for each of the one or more successive real-time images, e.g., until an image with a sufficiently high confidence metric is identified.

Any of the methods described herein, or steps thereof, may be embodied in non-transitory computer-readable medium comprising executable instructions, which when executed may cause a processor of a medical imaging system to perform the method or steps embodied herein.

DETAILED DESCRIPTION

Figure 1:
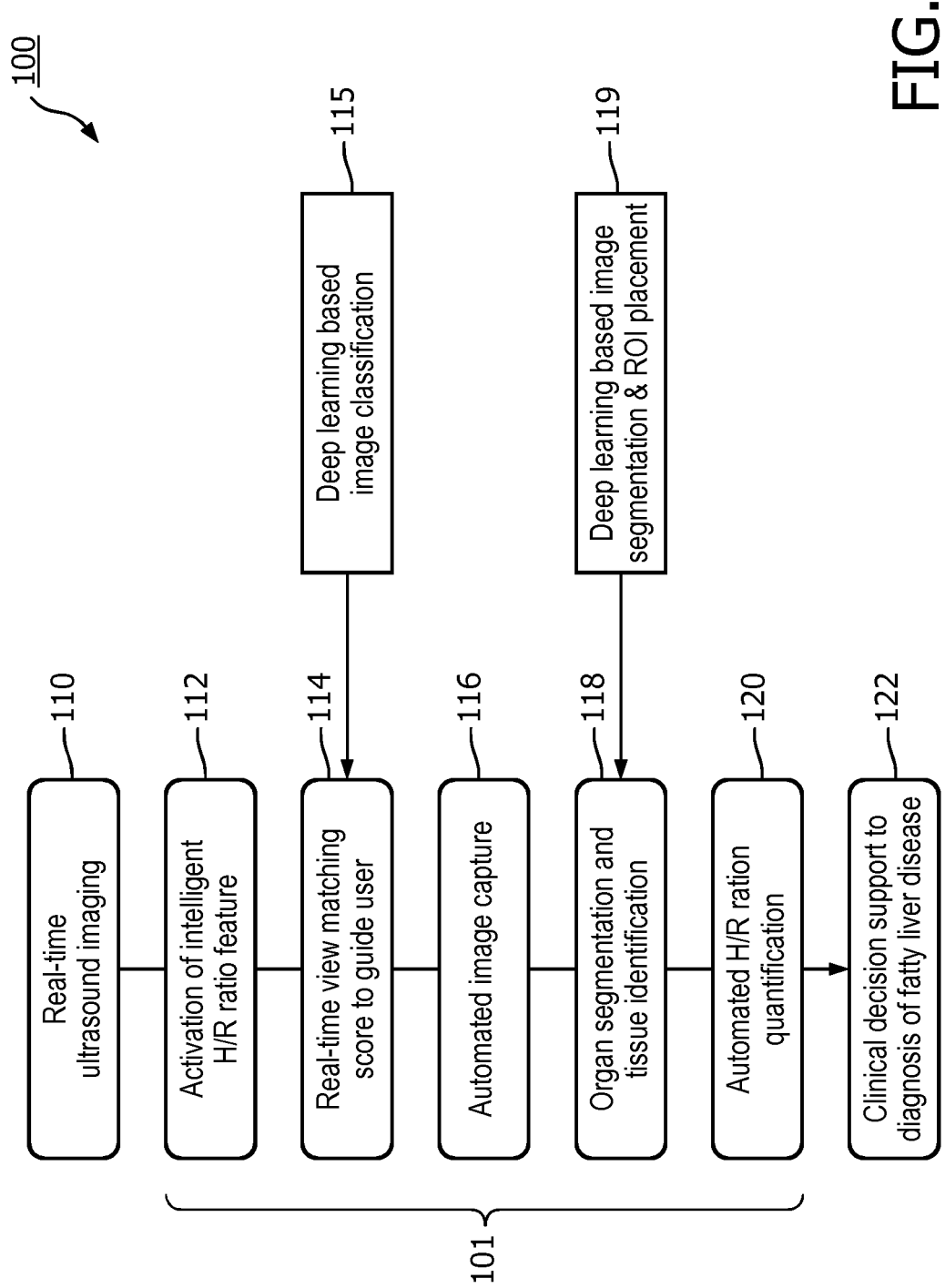
FIG. 1 shows a flow diagram of a process for ultrasonically inspecting biological tissue in accordance with some examples of the present disclosure.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Nonalcoholic Fatty Liver Disease (NAFLD) is the most common liver disease worldwide due to rising rate of obesity and diabetes. Fatty liver disease can lead to long term complications including nonalcoholic steatohepatitis (NASH) and liver fibrosis. If left untreated, it can further progress to life threatening stages—liver cirrhosis and primary liver cancer.

In current clinical practice, the gold standard for assessing liver disease is liver biopsy, an invasive procedure subject to sampling error and interpretation variability. MR proton density fat fraction (PDFF) is considered the new reference standard for NAFLD diagnosis as it can provide a quantitative biomarker of liver fat content. However MR-PDFF is an expensive diagnostic tool, which may not be available at every hospital. Ultrasound based hepatic renal echo-intensity ratio measurement (or simply hepatic renal ratio or H/R ratio) is a relatively simple and cost-effective method for fatty liver detection. Compared to MR, ultrasound is a real-time and costly effective imaging modality, more suitable for screening general population and low risk groups.

Generally, the ultrasound echo-intensity, for determining the H/R ratio, is calculated by selecting one region of interest (ROI) in the liver and one in the kidney cortex at the same depth, and by computing the ratio between the echo-intensities (e.g., using the average, mean, median or some other statistical value) of the two ROIs. Excessive fat infiltration in liver increases acoustic backscattering coefficient leading to higher grey scale values in ultrasound B-mode imaging. At a normal state, liver parenchyma and renal cortex have similar echogenicity. With more fat deposit, liver will appear more hyperechoic (i.e. brighter) than kidney cortex. While the usage of the H/R ratio in clinical practice is generally preferred over other proposed ultrasound methods for fatty liver diagnosis, because of its operator dependence and measurement variability, usage of the H/R liver has not yet been accepted as a routinely used clinical tool.

Ultrasound liver exams can be done at various locations on the abdomen, for example by placing the probe to acquire a subcostal or an intercostal view for scanning different areas of the liver (e.g., left lobe and right lobe). However, H/R ratio quantification requires a specific sagittal liver and right kidney view via intercostal scan. It is critical to have both organs in the field of view during ultrasound imaging. The boundary between the liver and right kidney should be placed near the center of the image. This image view may be relatively easy to obtain for a very experienced sonographer, but may be challenging (and subject to variability) among less experienced operators. Thus, H/R ratio measurement remains a very operator dependent process, as the optimal view may vary with the user performing the scan. Inter and intra operator variations can introduce measurement error and variability in evaluation of H/R ratio, leading to potential misdiagnosis. To make it a primary fatty liver screening tool, standardized and automatic measurement may be desirable for H/R ratio, especially for less experienced users in low resource settings. In accordance with the examples herein, an ultrasound system with intelligent liver scan interface is described which may reduce operator dependence and thus improve measurement reliability, for example improve the reliability of the H/R ratio quantification. In some embodiments, the system and techniques herein may be enhanced by the use of one or more properly trained neural networks.

In accordance with the examples herein, an ultrasound imaging system may be configured to aid the user in identifying and/or capturing a view suitable for H/R ratio quantification. The systems and techniques herein may be further configured to aid the user with process of H/R ratio quantification. As described, reliable H/R ratio computation relies on selecting a suitable view for H/R ratio quantification and on the correct placement of ROIs in liver and kidney parenchyma at the same depth to avoid depth-dependent echo-intensity attenuation. These aspects of the workflow may be particularly difficult for an inexperienced user, thus the system and methods described herein may automate one or more steps during a liver scan protocol to aid the user in appropriately selecting ROIs and performing H/R ratio computation.

FIG. 1 shows a flow diagram 100 of an example process for H/R quantification in accordance with the principles of the present disclosure. The H/R quantification processes may be performed in real-time, e.g., while the sonographer is acquiring the ultrasound image data. For example, during real-time ultrasound imaging (block 110), an intelligent liver scan mode may be activated (block 112), for example responsive to user input. In some examples, the user input to activate the intelligent liver scan mode may be generated, before or at the start of imaging, responsive to the user's selection of a graphical user control (e.g., see FIG. 3) or responsive to the operation of any other type of user control appropriately configured to invoke the intelligent liver scan mode. In other examples, the activation of the intelligent liver scan mode may occur responsive to different type of input such as responsive to specifying, for example in a text field, the nature of the scan (e.g., liver), responsive to a voice command, or automatically by the system determining the nature of the scan based on image data or other auxiliary data (e.g., patient history, previous patient exam). During the intelligent liver scan mode, the system may execute one or more sets of instructions as described in further detail below.

As shown in FIG. 1, during intelligent liver scan mode 101, the system may execute one or more sets of instructions for view matching, automated image capture, ROI identification, and echo-intensity ratio quantification. In the example process in FIG. 1, following activation of intelligent liver scan mode 101, the process continues with a view matching step (block 114), which concludes upon the identification of an image view suitable for H/R ratio quantification. During this process, the system may determine and/or output (e.g., for display to the user) a confidence metric, which is indicative of the live ultrasound image corresponding to a view suitable for H/R ratio quantification. As described a suitable view for H/R ratio quantification may be a sagittal liver/right kidney view and thus the system may be trained or otherwise configured to recognize whether the image corresponds to a suitable image view, also referred to as target image view. In some embodiments, the view matching sub-process may be performed or enhanced with one or more machine learning image classification models (block 115). In such examples, a machine learning image classification models (or classification neural network) trained to perform the appropriate image classification may be provided with one or more ultrasound images of the biological tissue (e.g., real-time ultrasound images of the patient's liver). The classification neural network may classify each incoming image into one or more classifications (e.g., "match," "match/no match," or any number of intermediate categories between match and no match indicating the quality of the match) and may output the classification or some other form of a confidence metric (e.g. a numeric value, which may be graphically displayed in a cold-hot color bar). In some examples, the process may automatically proceed to block 116 upon identification of an image that is classified as a match (e.g., without displaying the result of the classification). In other examples, the view matching process at block 114 may additionally or alternatively be performed by other image processing and classification techniques currently known or later developed.

The system may be configured to automatically capture (e.g., store in local memory) the image identified to represent a suitable image view (block 116) and to proceed to subsequent steps for H/R ratio quantification. For example, the system may perform image segmentation (block 118), e.g., using a conventional image processing technique or preferably using machine learning image segmentation model (block 119) to identifies regions within the image that correspond to the different types of tissue (e.g., liver and kidney). The segmentation may be used to identify a suitable view and/or for recommending placement of measurement ROIs. Upon identification of a suitable view, the system may automatically capture the view (i.e., without the user having to press the "acquire" button, which may improve the workflow and reduce the risk that the probe is moved as a result of the user having to press a button, and thus reducing the risk of the acquired image view deviating from the desired/target view. In some embodiments, the system may provide a notification of the desired view having been acquired (e.g., by an audible sound or by automatically transitioning to freeze mode and displaying the acquired view).

The system may then provide guidance, or automatically select, the ROIs for H/R quantification. For example, the system may identify one or more suitable pairs of locations for placing the first and second ROIs (e.g., the liver and kidney ROIs). The system may display the suitable pairs to the user (e.g., by displaying ROIs in a same pair using the same color to indicate pairing, or by displaying the pairs in sequence and allowing the user to scroll through the set of pairs) and await user selection of the pair of ROIs. Alternatively, the system may automatically select the pair of ROIs and proceed to block 120 for computing the H/R ratio. Suitable pairs of ROIs may be identified such that they are at the same depth in the image, such that the first and second ROIs are located in liver and kidney tissue, respectively, and such that the ROIs are not otherwise located in a region prone to imaging artifacts (e.g., too close or overlapping the boundary between the tissues, near or overlapping vessels or other non-uniform bodily structures). Additionally, the recommended ROIs may be defined by the system adaptively (e.g., based on the size and shape of the kidney cortex and liver) to ensure that the ROIs are placed in a location in the renal cortex (avoiding the renal sinus and medulla) and for the liver, ensuring that the ROI is placed in hepatic parenchyma free of vessels or lesions. Multiple ROI pairs may be suggested to the user to enable user selection, which may improve measurement accuracy, or in some cases H/R ratio quantification may be performed for multiple pairs of ROIs on the same image to achieve better measurement performance At block 120, the system computes the H/R ratio, for example by determining a representative value of the echo-intensities of each of the ROIs, such as the average, mean, medial or some other statistically suitable representation of the echo-intensities of all of the pixels in the ROI, and by taking the ratio of the two representative echo-intensity values. The computed H/R ratio may be stored along with the image, e.g., as an annotation on the image, as metadata appended to the header of the image file, as measurement archived in a report, or using any other suitable association, and the annotated/appended image may then be stored (initially locally, and at the completion of the exam, longer-term storage, for example in an external storage device) so that the imaging data and measurements can be used for clinical decision support (block 122).

As will be appreciated, the blocks and arrangement thereof in FIG. 1 are for illustration only and variations, such as combining, rearranging, adding, or removing blocks are contemplated. For example, although the process in FIG. 1 is illustrated in the context of real-time imaging, it will be appreciated that the process may be performed with previously acquired data. For example, upon activation of the intelligent liver scan features, the system may receive a set of previously acquired 3D image data of a volume of the subject which includes the liver and kidney, and the system may proceed to scroll through each slice in the 3D image data to identify the appropriate slice or MPR view that represents a suitable view of H/R quantification as described with reference to block 114. Once the appropriate view has been identified, the system may proceed to image segmentation and H/R quantification as previously described, and then store the extracted MPR view and computed measurement for subsequent diagnostic purposes.

In another example, the view matching and segmentation sub-processes may be combined, for example by using one or more neural networks trained to perform image segmentation. The image segmentation may be used at block 114 during the identification of appropriate view as the segmentation may be used to determine whether an image includes both types of tissue and a sufficient amount of the two types of tissue as needed for reliable H/R quantification. The image segmentation generated by the neural network(s) may then be subsequently used for ROI placement (e.g., for guidance or automatic selection by the system), as described with reference to blocks 118 and 119. In such scenarios, the machine learning image segmentation model of block 119 may be invoked earlier in the process (e.g., after block 112) and the incoming images (e.g., real-time image frames) may be provided to the neural network of block 119 for image view matching, which may eliminate the need for a classification model 115. In such scenarios, the automated image capture (assuming the process occurs during real-time imaging) may follow the image segmentation block 119. Any number of other variations or combinations are also possible and will be appreciated in view of the present disclosure.

Figure 2:
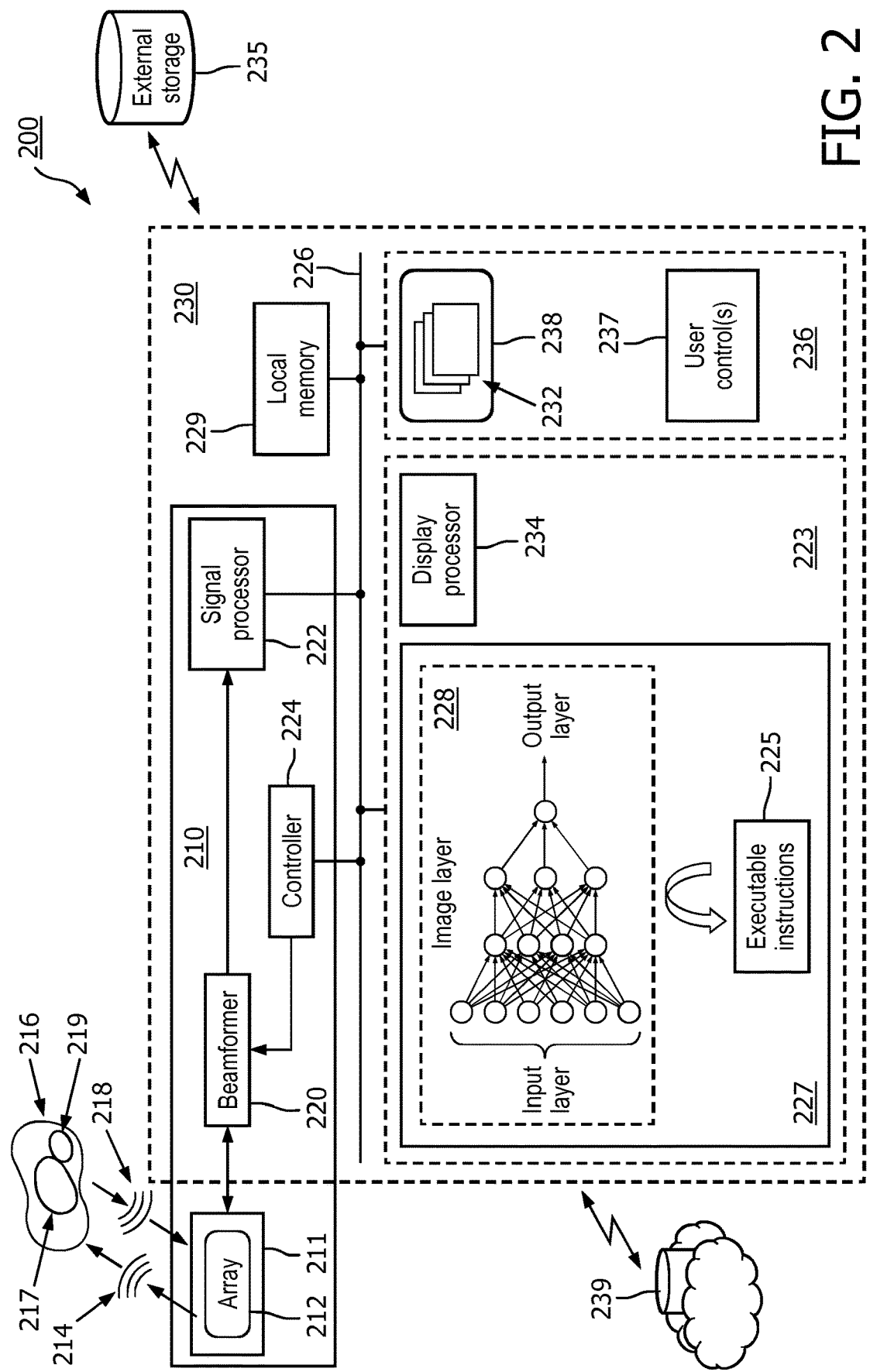
FIG. 2 is a block diagram of a system according to the principles of the present disclosure.

FIG. 2 shows a block diagram of a system 200 in accordance with some examples of the present disclosure. The system in FIG. 2 may embody, at least in part, and be used to perform the process 100 or any sub-processes thereof. FIG. 2 shows an ultrasound data acquisition unit 210 including an ultrasound transducer or probe 211, a beamformer 220, a controller 224, and a signal processor 222. FIG. 2 also shows a user interface 236 including a display 238, a memory 229, and at least one image data processor 223 all communicatively coupled to the ultrasound data acquisition unit 210, e.g., via a data bus 226. The components of system 200 and the arrangement thereof shown in FIG. 2 are illustrative only and variations, such as combining, rearranging, adding, or removing components are contemplated.

The ultrasound data acquisition unit 210 may be configured to acquire ultrasound image data 232, which may be displayed on the display 238 in real-time (i.e., as the image data is being acquired by ultrasonically scanning the subject). The ultrasound data acquisition unit 210 may include some or all of the components of a typical ultrasound scanner. For example, the ultrasound data acquisition unit 210 may include an ultrasound transducer or probe 211, which includes an ultrasound sensor array 212. The sensor array 212 is configured to transmit ultrasound 214 toward and detect echoes 218 from biological tissue 216, e.g., liver, kidney, breast, cardiac tissue or other types of biological tissue of a subject, for ultrasonically imaging the tissue 216. In some examples, the imaged tissue 216 may include at least two different types of tissue, e.g., liver parenchyma 217 and kidney parenchyma 219. A variety of transducer arrays may be used, e.g., linear arrays, curved arrays, or phased arrays. The array 212, for example, can include a two dimensional array of transducer elements capable of scanning in both elevation and azimuth dimensions for 2D and/or 3D imaging. The ultrasound data acquisition unit 210 includes a signal processor 222, which may be housed with the sensor array 212 or it may be physically separate from but communicatively (e.g., via a wired or wireless connection) coupled thereto. For example, the array 212 may be located in a handheld probe while the signal processor 222 may be located in the ultrasound system base 230, which in some cases may be embodied in a portable computing device such as a tablet.

The array 212 may be coupled to the system base 230 via a beamformer 220 configured to control operation of the array 212. In some embodiments the beamformer 220 may include one or more beamformers, (e.g., a microbeamformer in combination with a main beamformer in the ultrasound system base, or a combination of transmit and receive microbeamformers and/or main beamformers). The beamformer 220 may be configured to control the transmission of ultrasound and reception of echo signals by the array 212. In some embodiments, the beamformer 220 may include a microbeamformer, which may be co-located with the ultrasound array in the probe, and operating on groups of sensor elements for the transmission and/or reception of signals by the groups of sensor elements of the ultrasound sensor array 212. In some embodiments, the microbeamformer may be coupled to a transmit/receive (T/R) switch (not shown), which may be configured to switch between transmission and reception to protect the main beamformer from high energy transmit signals. In some embodiments, for example in portable ultrasound systems, the T/R switch and other elements of the system can be included in the ultrasound probe rather than in the system base 230. The ultrasound base typically includes software and hardware components including circuitry for signal processing and image data generation as well as executable instructions for providing a user interface. In some embodiments, the ultrasound probe may be coupled to the ultrasound system base via a wireless connection (e.g., WiFi, Bluetooth) or via a wired connection (e.g., a probe cable, which may be configured for parallel or serial data transmission).

The system 200 may include one or more processing components for generating ultrasound images from echoes detected by the array 212. For example, the system 200 may include a signal processor 222 may be configured to process the echo signals received from the transducer 211 for generating ultrasound images 232 and at least one image data processor 223 configured to present the ultrasound images on a display of the system. The ultrasound data acquisition unit 210 may include or be operatively coupled to a user interface 236, which may be integral with or otherwise physically connected to the system base 230 that houses the signal processor 222. In some embodiments, at least some components of the user interface may be wirelessly connected to the signal processor 222.

The user interface 236 may include a display 238 for displaying the ultrasound images 232 and in some cases, interactive graphical user interface (GUI) components. The user interface 236 may also include one or more user controls 237 for controlling operation(s) of the system 200. In some embodiments, the user control(s) 237 may include one or more hard controls (e.g., buttons, knobs, dials, encoders, mouse, trackball or others), which may be provided on a control panel of the system base 230. In some embodiments, the user control(s) 237 may additionally or alternatively include soft controls (e.g., GUI control elements or simply, GUI controls) provided on a touch sensitive display. The system 200 may also include local memory 229. The local memory may be provided by one or more hard disk drives, solid-state drives, or any other type of suitable storage device comprising non-volatile memory. The local memory 229 may be configured to store image data, executable instructions, or any other information necessary for the operation of system 200. In some examples, the system 200 may also be communicatively connected (via wired or wireless connection) to external memory, for example a picture archiving and communication system (PACS) storage device for longer term storage of image data and other patient information.

The signal processor 222 may be communicatively, operatively, and/or physically coupled to the sensor array 212 and/or the beamformer 220. The signal processor 222 may be configured to receive unfiltered and disorganized ultrasound data representing the ultrasound echoes 218 detected by the sensor array 212. From this data, the signal processor 222 is operable to generate ultrasound image data, which may be appropriately arranged, e.g., by processor 223, into images 232 for display. For example, the signal processor 222 may be configured to process the received echo signals in various ways, such as bandpass filtering, decimation, I and Q component separation, and harmonic signal separation. The signal processor 222 may also perform additional signal enhancement such as speckle reduction, signal compounding, and noise elimination. The signal processor 222 may then produce B-mode image data from the component signals such as by employing amplitude detection or any other known or later developed technique for the imaging of structures in the body. The B-mode image data may be further processed by scan conversion, e.g., to arrange the signals in the spatial relationship from which they were received in a desired image format. For instance, the scan conversion may arrange the signals into a two dimensional (2D) sector-shaped format, or a pyramidal or otherwise shaped three dimensional (3D) format. The B-mode image data may alternatively or additionally be processed by a multiplanar reformatter, which is configured to convert echoes which are received from points in a common plane in a volumetric region of the body into an ultrasonic image (e.g., a B-mode image) of that plane, for example as described in U.S. Pat. No. 6,443,896 (Detmer). The one or more processors of system 200 (e.g., processor 222 or 223) may additionally or alternatively generate a volume rendering of the B-mode image data (i.e. an image of the 3D dataset as viewed from a given reference point), e.g., as described in U.S. Pat. No. 6,530,885 (Entrekin et al.).

The signal processing and generation of image data may be performed in real-time as an operator ultrasonically scans the tissue 216 such that the image data may be displayed as real-time (or live) images of the subject. Alternatively, the images 232 may be generated from previously acquired image data stored in memory (e.g., local or external memory) associated with system 200. As described. the ultrasound data acquisition unit 210 may include a controller 224, which may be configured to set imaging parameters of the system 200, e.g., to control the transmission and reception of signals by the array 212, as well as certain signal and image processing functions of the system 200. The controller 224 may, among other thigs, control or set the imaging parameters of the system 200, which settings may be utilized by the beamformer 220 in controlling the excitation of elements of the array for the transmission and detection of signals by the array 212. Settings applied by controller 224 may also affect the signal and image processing of acquired ultrasound data, e.g., by controlling compressed dynamic range for display of images, or other image processing or display settings. As described, the transmission of ultrasonic pulses from the transducer array 212 under control of the beamformer may be directed by the transmit/receive controller, which may be coupled to the T/R switch and which may receive input from the user's operation of the user interface 236. Another function, which may be controlled by the controller 224, is the direction in which beams are steered, in the case of an electronically steerable array. Beams may be steered straight ahead from (orthogonal to) the transducer array 212, or at different angles for a wider field of view.

As shown in FIG. 2, the data acquisition unit 210 may be communicatively connected to at least one processor 223 configured to perform one or more of the functions associated with the intelligent (also referred to as computer-assisted, or AI-assisted) scanning of biological tissue, for example for performing an intelligent or guided liver scan, as described herein. The processor 223 may include one or more processing units (e.g., one or more single or multi-core CPUs, a single GPU or GPU cluster, or any arrangement of multiple processors configured for example for parallel processing) and uniquely configured to perform the functions described herein. For example, the processor 223 may be configured to receive a real-time image and to output a confidence metric for the real-time image, the confidence metric being indicative of a probability of the real-time ultrasound image visualizing the biological tissue in accordance with a target image view. In at least some embodiments, the processor 223 may employ at least one artificial neural network to generate the confidence metric. Upon determination that the confidence metric exceeds a threshold value, the processor 223 may be further configured to automatically capture (or store in local memory) the real-time ultrasound image, to determining locations of first and second regions of interest (ROIs), and to compute a ratio of the echo-intensity values of the first and second ROIs. The processor 223 may be further configured, if the confidence metric does not exceed the threshold value, to automatically receiving one or more successive real-time image frames and output a confidence metric for each of the one or more successive real-time image frames so as to continue the process of identifying a suitable image frame for echo-intensity ratio quantification.

In one example embodiment, the system 200 may be specifically configured for ultrasonically inspecting liver tissue, thus the biological tissue in the image frames may include at least a portion of hepatic tissue, renal tissue, or a combination of the two and the neural network may be specifically trained to produce a confidence metric which quantifies the probability of a given input image corresponding to a sagittal liver and right kidney view suitable for computing the hepatic-renal echo-intensity ratio. To that end, the neural network may be trained to determine the probability that the image should be classified into one or more of a plurality of categories including at least one category that is associated with a numeric value exceeding the threshold value. While examples herein are described in the context of liver imaging, it will be appreciated that the principles of the present disclosure may be applied to other imaging applications. For example, echo-intensity in biological tissue may be used to evaluate tissue composition, tissue homo- or heterogeneity, water and/or fat content in biological tissue other than the liver and thus may be used for tissue characterization or diagnosis in other application aside from the examples of hepatic imaging described in detail herein.

In addition to performing functions associated with intelligent scanning of biological tissue, the processor 223 may be configured to provide other functionality associated with the display of image data are related information. In some embodiments, he processor 223 may include a display processor 234, which may additionally include functionality for generating and causing the display 238 to present annotations along with the image data, graphical indicators such as to provide feedback during view matching, and/or any of the graphical user interface components associated with the intelligent scanning mode of system 200. For example, the display processor 234 may receive the image data for further enhancement, buffering and temporary storage before being displayed on display 238. The display 238 may include a display device implemented using a variety of known display technologies, such as LCD, LED, OLED, or plasma display technology. While the engine 227 and display processor 234 are shown as separate components in FIG. 2 for illustration, in practice the functionality of these components (and any other processing components described herein) may be integrated into a single processor or a cluster of processors arranged to operate together (e.g., in parallel).

As will be further described, the processor 223 may include an echo-intensity ratio quantification engine 227, which may be embodied in any suitable combination of software (e.g., executable instructions in the form of source code or compiled/machine instructions) and hardware components (e.g., one or more processors programmable by the executable instructions and/or hard-wired circuitry such as application specific integrated circuits ASICs specifically programmed to perform one or more of the functions of engine 227). The engine 227 may include functionality for preforming one or more of the steps described with reference to FIG. 1. In some examples, the functionality of engine 227 may be implemented via processor-executable instructions 225, which when executed by processor 223 configure or program the processor to perform the functions associated with identifying an appropriate view for imaging and/or quantifying the echo-intensity ratio of the two RIOs. In some embodiments, as described further herein, the engine 227 may include at least one artificial network of neural perceptrons 228 (also referred to herein as artificial neural network or simply neural network), trained to perform one or more of the functions of engine 227. Any suitable types of machine learning algorithms (e.g., generative, discriminative, or combinations thereof) and/or architectures may be used to implement neural network 228. In some examples, the neural network 228 may include a deep neural network, more specifically a deep convolutional neural network, which may be trained to perform image classification, image segmentation, image comparison, or any combinations thereof. With the increasing volume of stored medical image data (e.g., in PACS or in cloud storage) and often annotated image data which can provide the labeling needed for training images, the availability of high-quality clinical images is increasing, which may be leveraged to train a neural network to perform classification, segmentation, object recognition, or other image processing tasks on medical image data. It will be understood that training images need not include full images produced by an imagining system but may include patches or portions of a medical image of the relevant target biological tissue or organ.

The neural network 228 may have any suitable architecture, and thus include any number of layers of input, output and hidden nodes in any suitable arrangement (e.g., layers of convolution, normalization, pooling, and/or dense or fully connected layers). In some examples, the network 228 may include any suitable arrangement of one or more subnetworks forming a larger network trained to produce the desired result(s). In yet further examples, the neural network 228 may be operatively associated with additional programming, e.g., to perform pre-processing of the data to be input to the neural network 228 and/or post-processing of the output of the network 228 to produce the appropriate result from the echo-intensity ratio quantification engine 227.

As described, some or all of the components of system 200 may be co-located (e.g., within a system base 230) and communicatively connected (e.g., via a data bus 226). Additionally or alternatively, components of the system 200 may be connected to remote components via one or more wired or wireless connections. For example, the system base 230 may additionally be communicatively coupled to external storage 235, e.g., an external drive or a PACS storage device of the medical facility. In some embodiments, some or all of the functionality of engine 227 may reside in a remote computing device 239, such as a cloud server. For example, the one or more neural networks 228 may reside and be executed on the remote computing device 239 with the system base 230 (for example a portable system such as a tablet U/S imagine system) configured to transmit the live images to the cloud for classification and/or segmentation and to receive the output of engine 227 (e.g., a confidence metric) for display along with the relevant image data acquired by probe 211.

Figure 3:
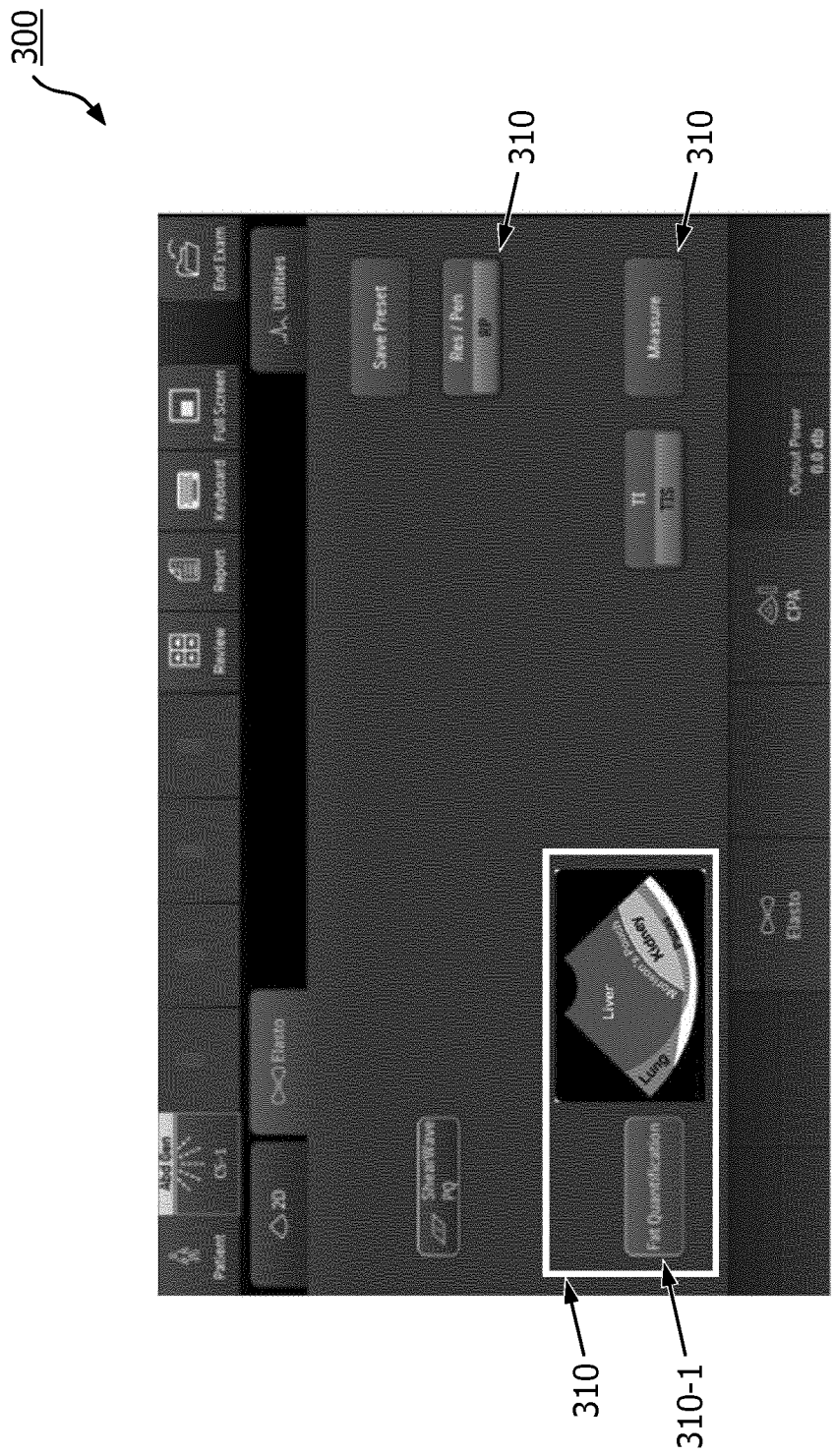
FIG. 3 is a screen capture of a graphical user interface provided by an ultrasound system in accordance with some examples herein.

As described herein, the processor 223 may be configured to identify a view (e.g., from the incoming real-time images) that suitable for echo-intensity ratio quantification (e.g., in the case of liver imaging for fat quantification using the H/R ratio), and to automatically capture the identified suitable view for further processing associated with computing the echo-intensity ratio, which processes are collectively referred to as intelligent scanning or AI-assisted scanning. FIG. 3 shows an example of a graphical user interface (GUI) 300, which may be used to activate an intelligent scanning mode of an ultrasound imaging system according to the examples herein and thus invoke the associated functionality of processor 223. The GUI 300 may be provided on a touch sensitive display of an ultrasound system (e.g., system 200) and include one or more interactive GUI elements of controls 310 for selecting or activating functions of the system. For example, the GUI 300 may include a control 310 (e.g., a fat quantification soft button) for activating an intelligent scanning mode 301 (AI-assisted liver scan) of system 200. Any number of such controls may be provided for activating any number of AI-assisted functions of system 200. Once operating in intelligent scanning mode, the system may provide guidance to the user or automate certain operations of the respective scanning protocol.

Figure 4:
FIG. 4 shows additional icons, or other user interface elements provided on a display of an ultrasound system in accordance with some examples herein.
Figure 4:
Figure 4:
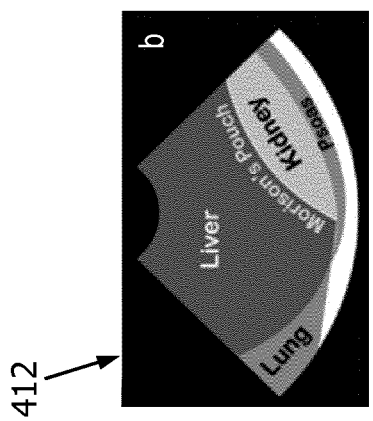

In some example, the system may guide the user in acquiring the appropriate view of the tissue. FIG. 4, panels a-c shows additional graphical displays that may be provided during the AI-assisted liver scan. For example, upon activation, via control 310-1, the system may display, e.g., in a new window on the touch sensitive display or on the main display, one or more guidance icons, such as icon 410 (FIG. 4, panel a), which includes a graphic designed to guide the user in placement of the probe to acquire the appropriate anatomical view. The system may additionally or alternatively display an icon 412 (FIG. 4, panel b), which may be a graphic illustrating the relative position of the organs in the desired anatomical view. The icon 412 may aid the user (particularly an inexperienced user) to visualize the optimal view prior to or while performing the scan. One or more of the icons 410, 412 may be displayed once at the start of the scanning session or they may be displayed concurrently (e.g., in reduced/thumbnail format) on the display while the user is scanning and the system is displaying the real time images 422 in the active area 420 of the display (FIG. 4, panel c). Once the operator applies the probe to the patient and acquires an acoustic window, the system may automatically activate the live image display (e.g., as shown in panel c), and the system may begin displaying real-time or live images of the subject. In some embodiments, the system may provide additional guidance while the system perform image view analysis in the background, such as to provide instructions to the user on how to manipulate the probe (e.g., by visual or audio instructions to the user to move the probe along the sagittal plane or toe-heel the probe to better capture the desired tissue within the probe's field of view).

During intelligent scan mode, the image data for each acquired frame may be provided to the engine 227 for identification of a suitable view in real-time. As described, the view identification (or view matching) may be performed by a neural network 228, which may include one or any number of stacked, connected or otherwise appropriately arranged networks of artificial neurons. In some examples, the neural network 228 may include a deep convolutional network configured to output, for each input image, a confidence metric (also referred to herein as matching score). The confidence metric (or matching score) may provide an indication of a probability or confidence level that the given image corresponds to the desired or target image view. The matching score may be derived, at least in part, through classification, segmentation, object detection, or other technique(s) for analyzing the content of the image or any suitable combinations thereof. In some examples, the deep convolutional network may include a fully convolutional network trained to perform image segmentation. In some embodiments, the deep convolutional network may include at least one convolutional subnetwork configured to perform object detection image segmentation, or both and optionally at least one additional subnetwork configured to classify the output of the object detection or segmentation network to generate the confidence metric. In some examples, a fully convolutional network may be particularly well suited for machine learning of image segmentation as such networks are well suited for dense (or pixel-by-pixel) prediction and thus can be effectively trained to partition an image into multiple segments of related pixels.

Figure 5:
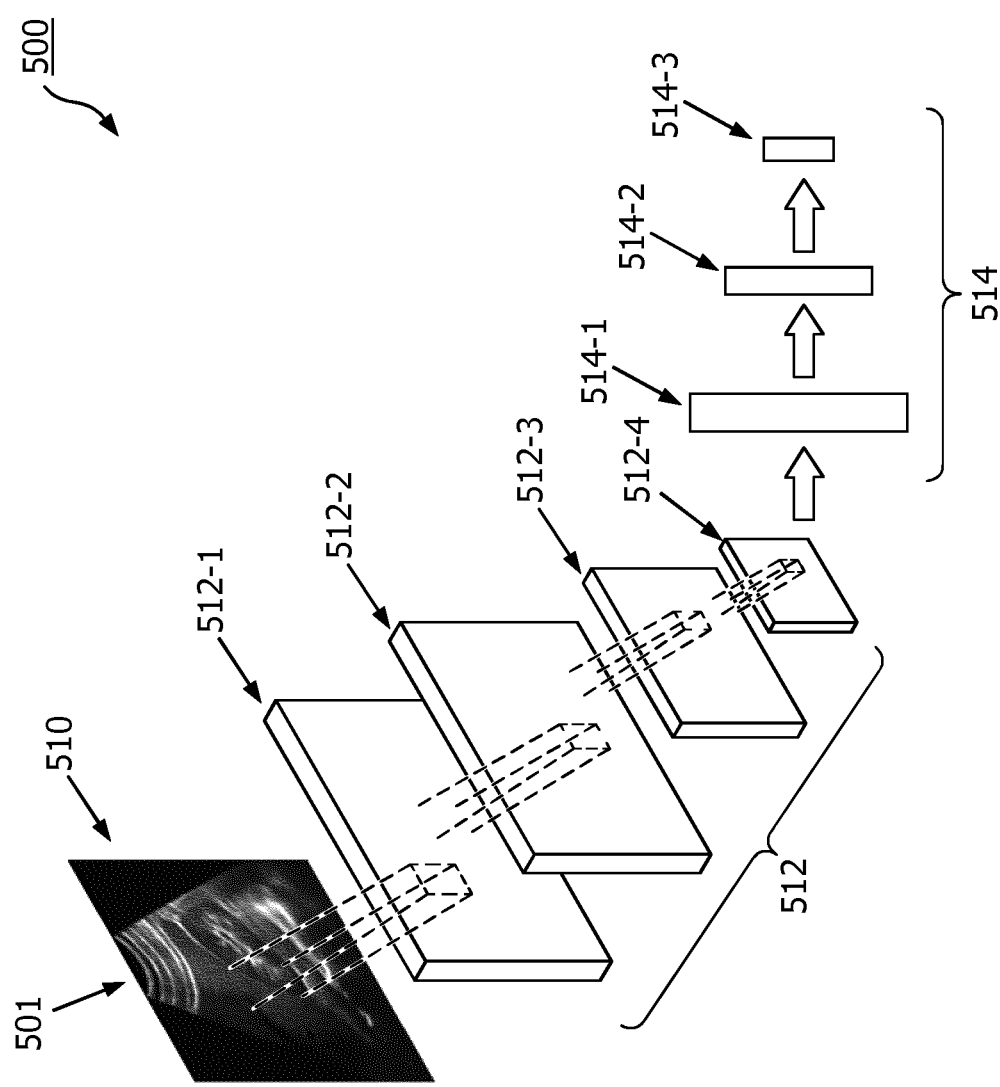
FIG. 5 shows an illustration of a neural network architecture according to some examples of the present disclosure.

In one example, the network 228 (e.g., a deep convolutional network) may be trained to perform image classification to classify each input image into one of a plurality of categories. A deep convolutional network may include an input layer, which receives the input image, an output layer, which outputs the classification (e.g., a binary classification or a vector listing the probabilities of the input image being associated with any one of the classification categories), and any number of intermediate layers including convolution, pooling, regularization and fully connected (or dense) layers. FIG. 5 shows an example architecture of a convolutional network that may be used in some examples of the present disclosure. The network 500 includes an input layer 510, four convolution layers 512, each associated with one or more regularization and pooling layers, and two to four, in this specific case three, fully connected layers 514, with the last being the output layer 514-3, although in other examples, the network may include a different number of layers for example fewer or greater number of convolutional layers and/or fully connected layer depending on the complexity of the dataset for example. The input layer 510 is configured to receive an input image 501, e.g., an ultrasound image visualizing hepatic and/or renal tissue. The image 501 may be a single or a multi-channel (either grayscale or color) image. In the illustrated example, the input image 501 is a 3-channel gray scale image with 150×150 pixel resolution and thus the input volume to the network 500 is a three dimensional array of pixel values having the size 150×150× 3, although it will be appreciated that the input size may be different in other examples (e.g., accepting images of 128× 128, 256×256, or any other resolution). At each convolution layer, multiples filters are convolved on the input image to produce the output of each convolution layer, which is a stack of feature (or activation) maps (e.g., 32 at layer 512-1, 16 at layer 512-2, 8 at layer 512-3, and 4 at layer 512-4. Following convolution layers with pooling, the input size in the spatial dimension is reduced (e.g., from 150 to 75, then to 37), this down sampling being dependent in part on the type of pooling (e.g., max, average, L2-norm or other), the convolution stride, and the pooling stride. In the specific example shown, the input image is processed to a stack of 4, 37×37 activation maps at the output of the last convolution layer 512-4, which is then provided to the first fully connected layer 514-1, which outputs a 32-size vector. The output of the first fully connected layer 514-1 is then propagated through two additional fully connected layers 514-2, 514-3 having output sizes of 16 and 2, respectively, to output, at the last fully connected (or output) layer 514-3, a two-dimensional vector where each dimension represents the probability of the image falling within either of the two or binary classification (e.g., match or no match) categories. It will be appreciated that the particular architecture shown in FIG. 5 is provided for illustration only and the specific architecture, number of layers and input and output sizes may vary in other examples. For example, in other embodiments, the network 500 may be trained to output a classification vector (at the output layer 514-3) of a different size such as with 4, 5, 6 or a greater number of classification categories.

Figure 6:
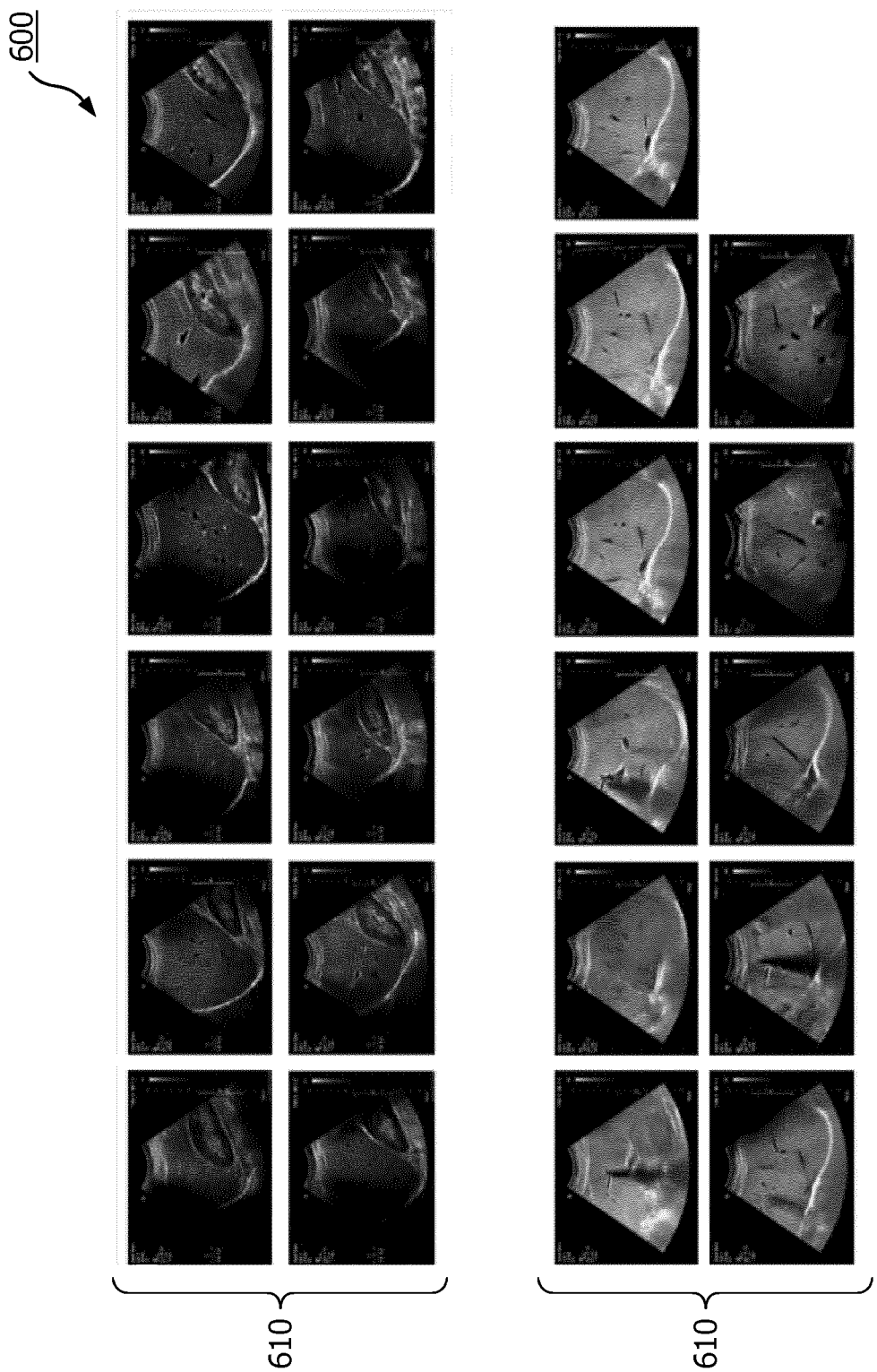
FIG. 6 shows training data examples in accordance with the principles of the present disclosure.

In the case of binary classification (i.e., match or optimal view and no match or sub-optimal view), the network may be trained using a set of labeled images, also referred to as training data. The training data may include a large number (e.g. from hundreds to thousands of clinical images) in which each image has been labeled (e.g., by an experienced sonographer or clinician) as either a match (or optimal view) or no match (sub-optimal view). FIG. 6 shows an example of images 600, which may be used as training data. The set of images 610, each of which visualize a sufficient amount of both liver and kidney tissue, may be labeled as belonging to the "match" classification category. The set of images 612, which primarily show liver tissue or otherwise unsuitable for H/R ratio quantification, may be labeled as belonging to the "no match" classification category. The training data 600 is provided to the neural network and the network's parameters are updated (e.g., through back-propagation or other technique) throughout the training process. In one experimental version of the neural network 500, more than 5,400 clinical images were used for training and validation. The training images were split into a training set and a testing or validation set. The training and validation dataset include labeled images which are provided to the network for training. Labeled test images, which were never shown to the network during training, were used for testing the performance of the system, which in experimental use was shown to provide at least 85% accurate predictions. In such manner, a neural network, such as network 500 may be trained to classify a new unknown image in one of the classification categories for which the network has been trained.

As will be appreciated, the network 500 may be trained to classify the input image into more than two categories. For this scenario, the network may be trained with images labeled into more than two categories, such that all categories being trained are represented in the training data. For example, the training data may include images representing no match (e.g., images that do not include both liver and kidney parenchyma in the view) and thus labeled with a value of 0, and images that include the ideal positioning of the liver and kidney within the image, which may be labeled as a match (or optimal view) and/or assigned a value of 1. The remaining images that fall somewhere in between an optimal and unacceptable view may be divided into any number of intermediate categories, and correspondingly labeled with a value between 0 and 1, to indicate the quality of the match, for example with any images that do not include any kidney tissue, for example poor match (0.2), acceptable match (0.4), good match (0.6), and very good match (0.8). The intermediate classifications of the training images may be based in part on the quality by the view as judged by an experienced sonographer or clinician or by quantitative assessment such as by computation of the percentage of liver and kidney tissue being visualized in the image, location of the boundary between the liver and kidney, etc.

Figure 7:
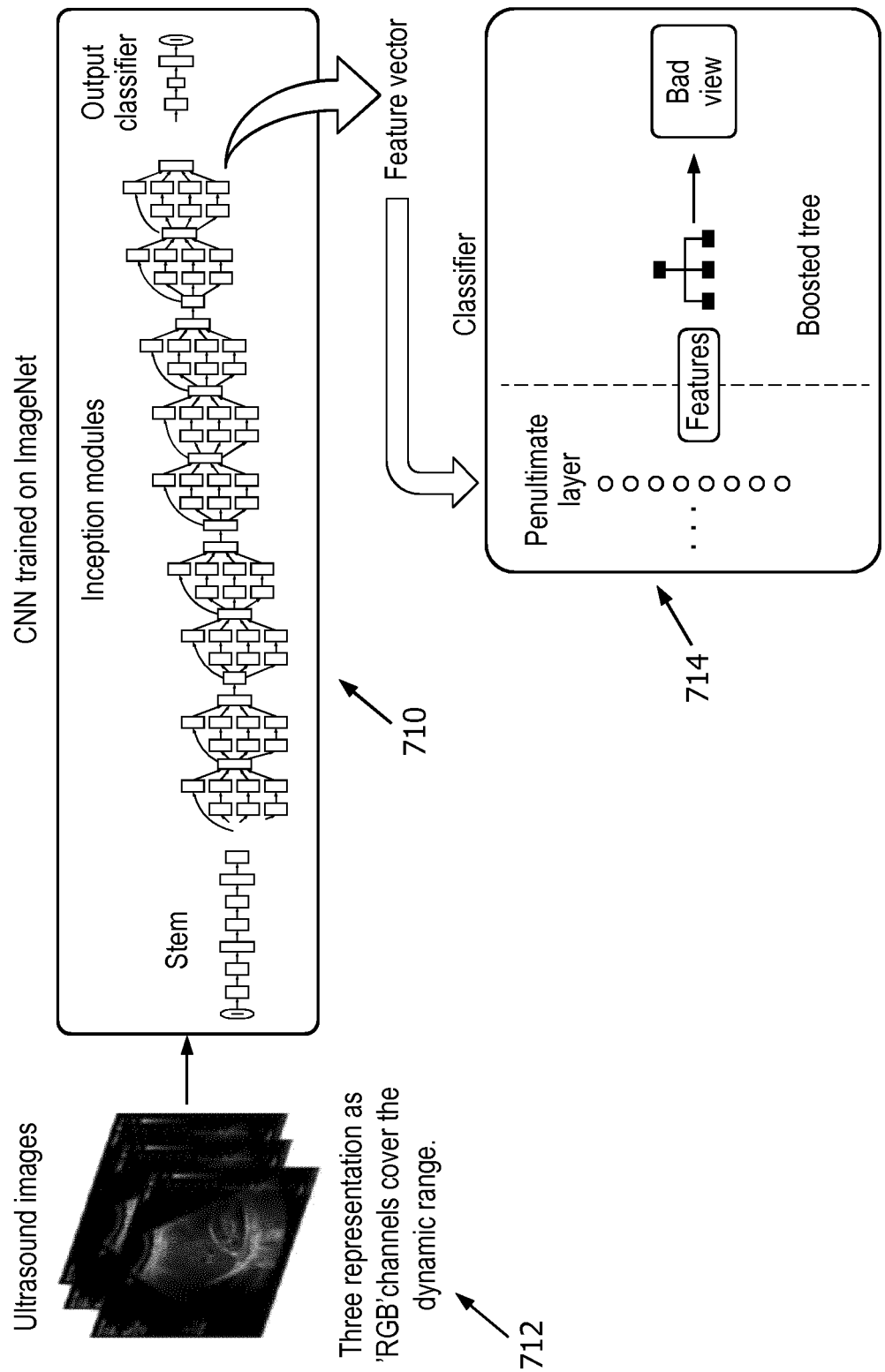
FIG. 7 shows an illustration of a method of training a neural network according to some examples of the present disclosure.

For training a neural network according to the present disclosure, any suitable architecture, such as a VGGNet-like or ResNet-like architecture, may be used and the "blank slate" network may be trained from scratch (i.e., without any preconfiguration of the weights). As shown in FIG. 7, to reduce the amount of training data needed, a pre-trained network, such as the Inception V3 (as shown in FIG. 7) or another network may be used as a starting point. The pre-trained network 710 may then be fine-tuned specifically for classifying medical image data with a much smaller training data set of medical images (e.g., ultrasound images 712) of the particular clinical application, in this case liver imaging. Fine-tuning may be performed, for example by feeding the penultimate layer of the Inception V3 network into a new output classifier 714 (e.g., comprised of fully connected layers) and configured to produce the desired classification (e.g., match/no match), or by providing the feature vector output by the Inception V3 network into a new classifier, which requires less training data.

As described, upon identification of a suitable view the system may automatically capture (e.g., store in local memory) the image that represents the suitable view. The identification of a suitable view may be based on the engine 227 outputting a metric or score indicative of a match. For example if a given image is classified as being 75% or more within the category of good view and 25% or less in the category of bad view, the system may determine that the input image corresponds to a suitable view. Similarly, in the case of non-binary classification, the system may compute a view matching score, for example by summing the probabilities of each classification weighted by the classification value. For example, if the network is trained to classify an image into n categories, each associated with a unique value between 0 and 1 for example, and the network is configured to output a classification vector $y$ ($c_1, c_2, \ldots c_n$), which may represent the probabilities of the image corresponding to the respective categories, the engine 227 may be configured to compute a view matching score M by summing the weighted values of the classification vector, i.e., $M = \Sigma_1^n n*(c_i)$. The engine may be configured to determine that the view is a match (e.g., suitable for quantification) if the view matching score exceed a threshold value (e.g., 0.5, 0.65, 0.70 or greater). In other examples, the system may be configured to determine that the view is a match only if the probability of the either the very good or optimal classification exceeds a certain value (e.g., 50% or greater).

In some embodiments, the matching may be performed in the background, and may be substantially transparent to the user. In some such examples, while the user manipulates the probe and the display continues to display the real-time time images, no other information generated by the view matching process is provided until the system identifies a suitable view. Upon identification of the view, the system may enter freeze mode with the image representing the suitable view displayed (in freeze mode) on the display. The automatic activation of freeze mode may provide an indication of the identified suitable view.

During the intelligent scanning mode, the system may provide guidance to the user to aid the user in acquiring the suitable view (e.g., in the form of instructions to aid the user in manipulating the probe). In some embodiments, the system may provide guidance such as by displaying a graphical indicator that represents the current value of the confidence metric being computed by the system's processor (e.g., processor 223).

Figure 8:
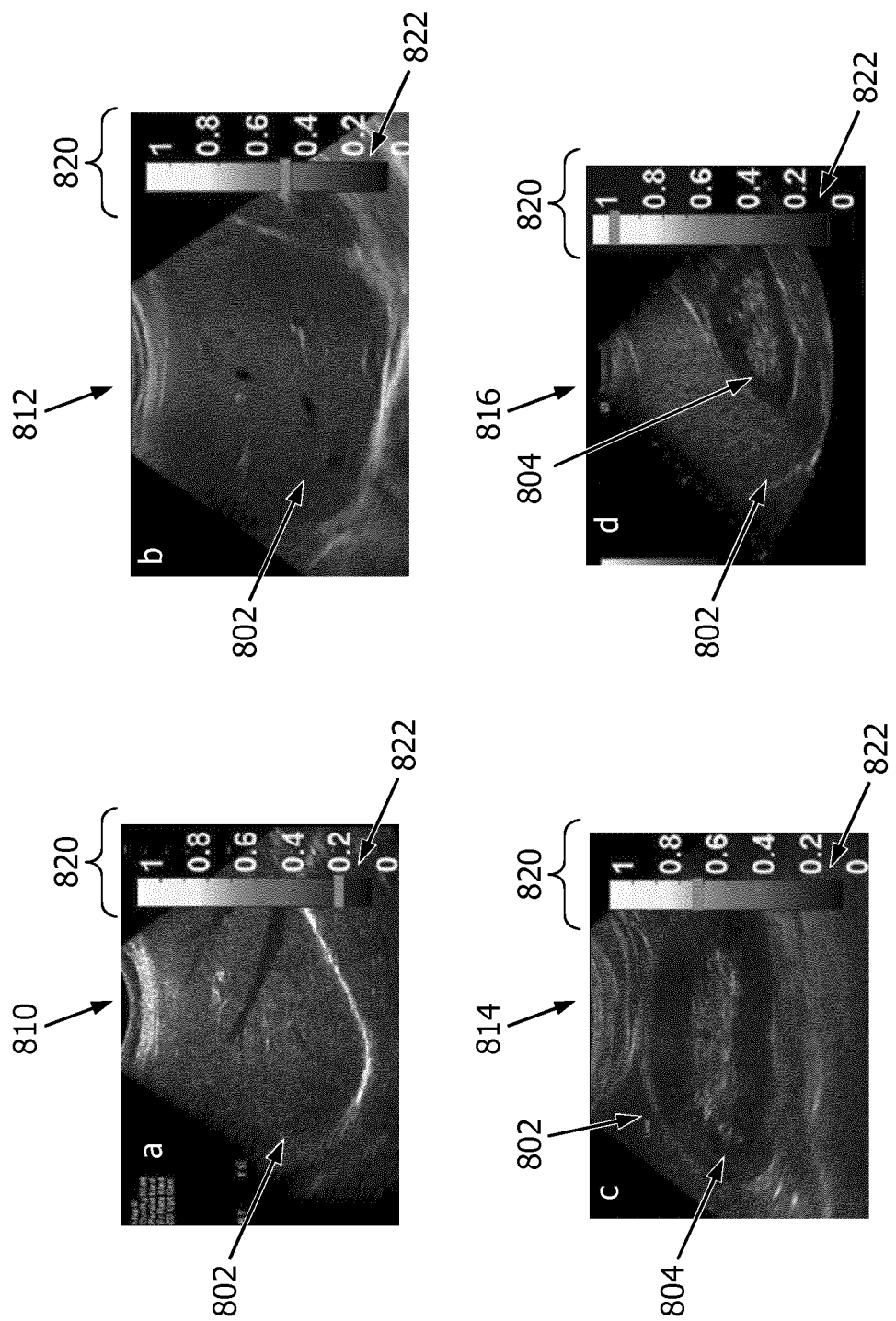
FIG. 8 shows screen captures of an ultrasound system display, which include graphical indicators in accordance with the principles of the present disclosure.

FIG. 8 shows example screen captures of an ultrasound system with graphical indicator, which may be dynamically updated in order to provide a real-time visual indication of the confidence metric of any given live image. In this example, the graphical indicator is implemented as a match indicator 820 in the form of a color bar (e.g., hot-cold color bar, with the hot or red color corresponding to a match and cold or blue color corresponding to a no-match) with a movable gage. Each of the panels a-d of FIG. 8 show screen captures of live ultrasounds images 810, 812, 814, and 816, of liver tissue 802 and each live image is concurrently displayed with a color bar match indicator 820. The match indicator 820 includes a dynamic component 822 (e.g., a sliding level or bar) which moves up and down the color bar to indicate the value of the view matching score for the image frame currently being displayed. The minimum and maximum values may correspond to the minimum and maximum values of the classification categories, in this case 0 to 1, and the dynamic component 822 may represent the computed or otherwise derived view matching score. As shown, in the image 810, the view matching score is around 0.2, which indicates a relatively low match probability to reflect that no kidney tissue is included in the view. As the user manipulates the probe, the system continuously recalculates the view matching score for successive frames and dynamically updates the position of the dynamic component 822 along the color bar, which the view in image 816, associated with the highest of the four view matching scores, representing the best of the four views shown in FIG. 8. As described, in a preferred embodiment, the view matching score is produced responsive to operations of a neural network; however, the view matching score may be obtained additionally or alternatively using traditional computer vision approaches and/or handcrafted features generation (e.g., canny edge detection, histogram of oriented gradients, and support vector machines). In other examples, the match indicator may be implemented using a different type of graphical element, such as a speed dial with the zero speed corresponding to the minimum value of the confidence metric and the maximum speed on the dial corresponding to the maximum value of the confidence metric, the arrow in the dial dynamically updating to indicate the current value of the confidence metric. In yet further examples, the confidence metric may be numerically displayed along with the image. Other graphical indicators may be used to visualize the confidence metric on the display.

In some embodiments, the view matching may be performed using image segmentation. For example, referring back to FIG. 2, the one or more neural networks 228 employed by system 200 may be trained to segment the input image and make a determination, based on the segmentation of the image, of whether the image corresponds to the target view (e.g., whether the image contains the target arrangement of tissue/organs within the view). The network 228 may include any number of layers (e.g., convolution, pooling, and regularization layers) trained to produce a segmentation map of each input image. As with non-machine learning techniques, the process of segmentation partitions a digital image into multiple regions or segments (i.e., sets of pixels or voxels in the case of 3D image data). In specific examples, the network 228 may be trained to perform pixel-wise semantic segmentation thereby assigning each pixel in the image into one of a plurality of categories (e.g., liver, kidney, lung, Morrison's pouch, vessel, lesion, etc.).

Figure 9:
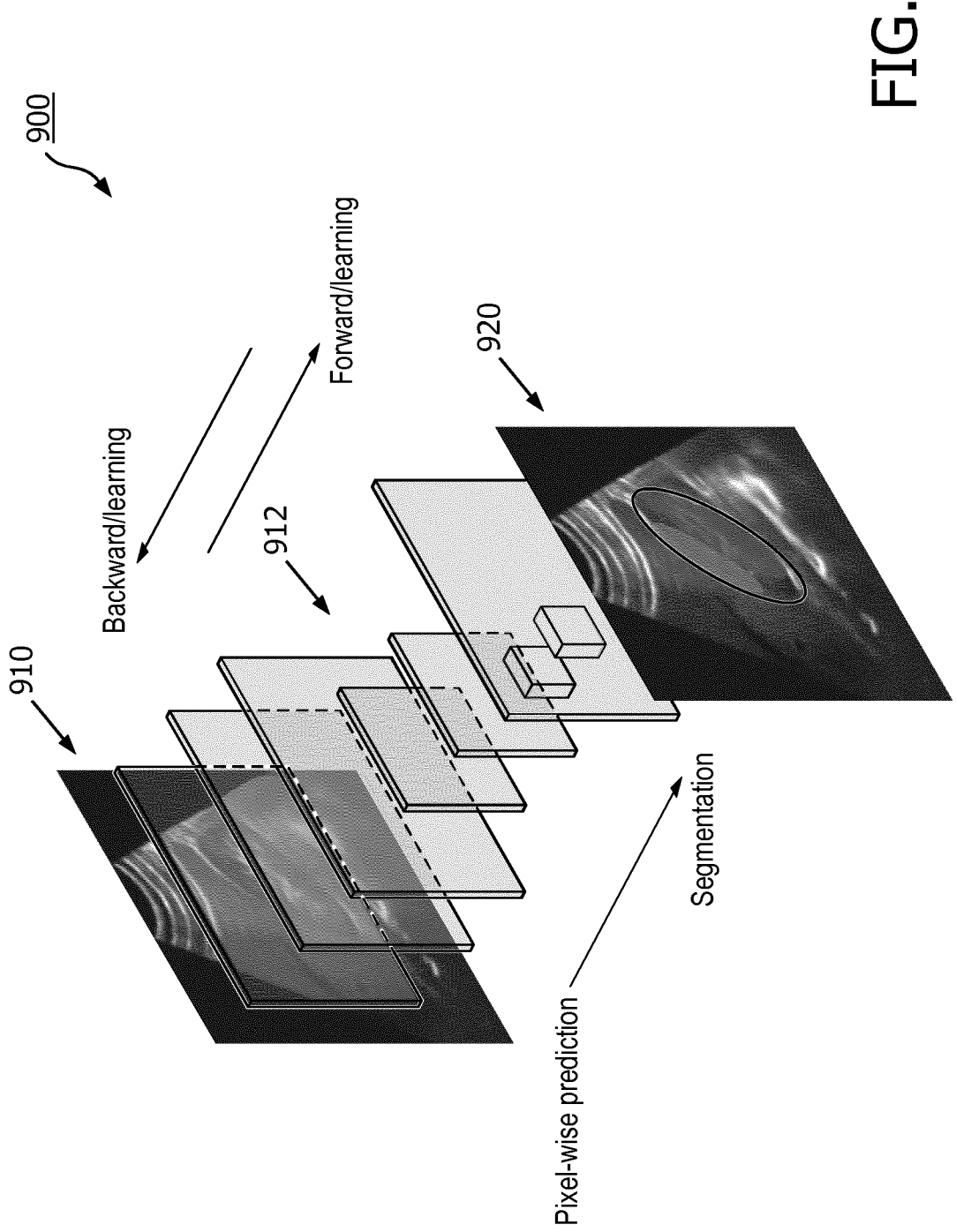
FIG. 9 shows an illustration of a neural network architecture according to further examples of the present disclosure.
Figure 10A:
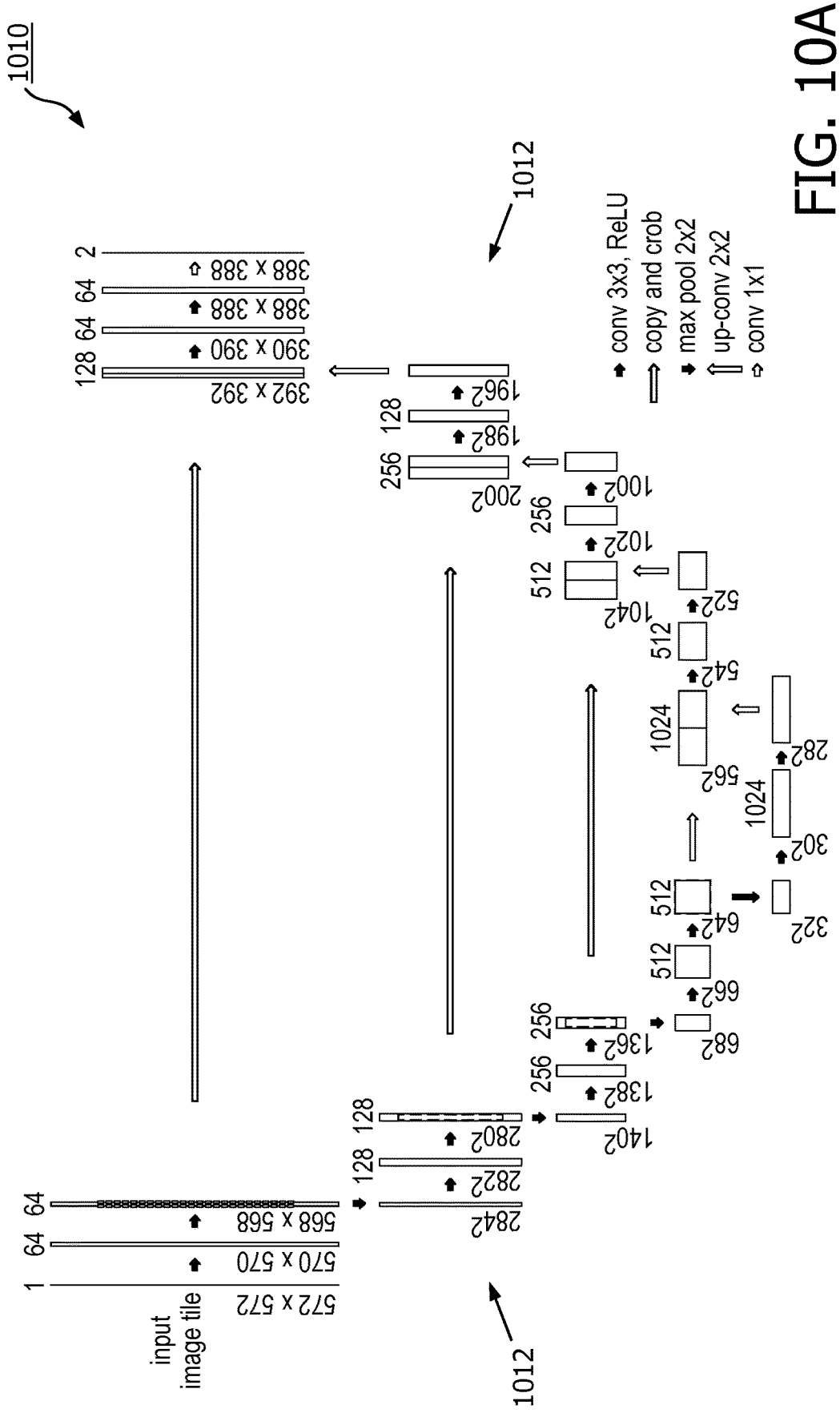
FIGS. 10A and 10B show illustrations of additional neural network architectures that may be used to implement examples of the present disclosure.
Figure 10B:
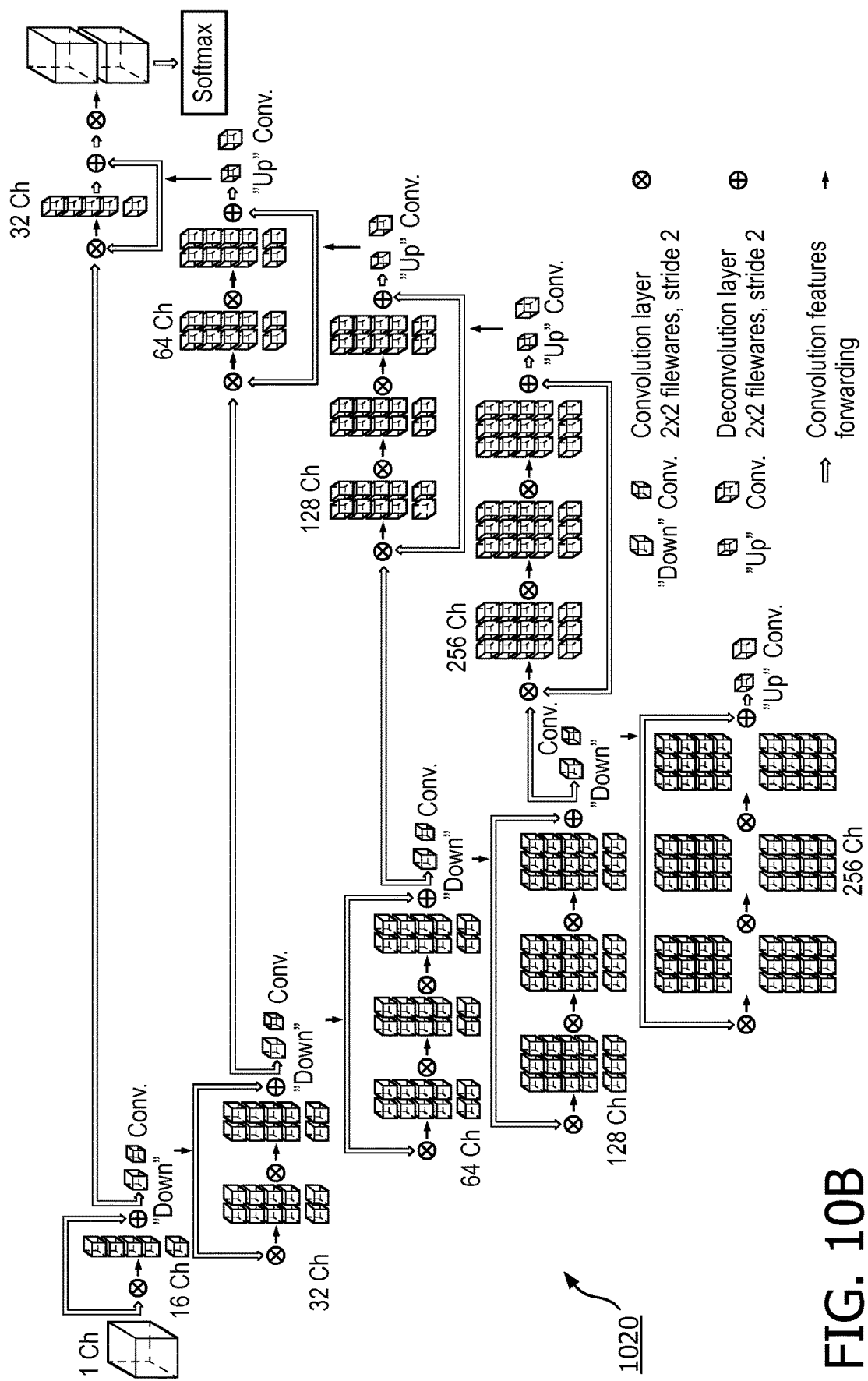

FIG. 9 shows an example of a fully-convolutional neural network 900, which may be trained to perform image segmentation. The network 900 may be trained, using training data that includes labeled images (e.g., images of the liver and/or kidney overlaid with the boundaries, delineated either manually or with computer assistance, of the different types of tissue). The network 900 may thus be trained to segment an input ultrasound image to produce a segmentation map, in which groups of adjacent pixels determined by the machine-learning algorithm to be associated with a same category (e.g., a same tissue type) are assigned to the same semantic category. The segmentation map may be constructed from a plurality of segmentation masks, each of which corresponds to one of the plurality of categories. All of the pixels in a given segment (or super pixel) are assigned the same pixel value (either grayscale or color) and the final segmentation map is assembled by combining the super pixels into a single map (see e.g., segmentation map 920). The network 900 may be used to implement, at least in part, the network 228 of FIG. 2. The network 900 may be implemented as a convolutional auto-encoder with skip connections from encoder layers to decoder layers that are on the same "level". Examples of such architecture are the U-net architecture 1010 shown in FIG. 10A suitable for segmentation of 2D images, and the V-net architecture 1020 shown in FIG. 10B, well suited for segmentation of 3D image data. As shown in FIGS. 9 and 10, such network may include a contracting path (e.g., path 1012 in FIG. 10A) followed by an expanding path (e.g., path 1014 in FIG. 10A) with cascade of convolutional and max pooling layers. The contracting path down samples the image data in the spatial dimension and the expanding path up samples the data to the original image size. In embodiments in a machine learning image segmentation is utilized, such neural network may include a symmetric, fully convolutional network with the same number of down-sampling convolutional layers along the contracting path as the number of up-sampling layers along the expanding path, for example as shown in FIGS. 10A and 10B.

Other types of deep convolutional neural network may be trained to segment an input image and generate a segmentation map, such that a confidence metric may be computed based, at least in part, on the segmentation map of a real-time ultrasound image. In some embodiments, the computation of the confidence metric, when using segmentation, may involve comparing the segmentation map output by the neural network to a segmentation map of the desired view. In some embodiments, the neural network may include a plurality of subnetworks, one of which may be trained to perform segmentation, and another one of which may be trained to compute the confidence metric, e.g., by classifying the segmentation map into classes which correspond to the quality of the match. In one such example, the first subnetwork may receive the input image and perform segmentation to produce a segmentation map. The segmentation map may be provided to a second subnetwork (e.g., a convolutional classification algorithm or another type of convolutional network) which is trained to recognize whether the segmentation map corresponds to the target view (e.g., an optimal sagittal liver/right kidney view). In yet other examples, the confidence metric may be computed by quantitatively analyzing the content of the segmentation map alone (i.e. without comparison to an optimal map), such as to determine whether the map, and thus the source image, contains a sufficient amount of a particular type of tissue (e.g., kidney tissue) and/or the image visualizes the particular type of tissue in the appropriate location within the image.

As illustrated in FIG. 9, the network 900 may be configured to receive an input image (e.g., ultrasound image 910 of the liver) and trained to perform pixel-wise predictions to derive the segmentation map 920. For example, the network 900 may be trained to classify each pixel of image 910 into one of a plurality of segmentation categories or masks (e.g., liver, kidney, lung, and background, or other combinations, for example additionally segmenting the kidney cortex from the kidney medulla). For training, the network 900 may be provided with multiple training images, each of which has been appropriately labeled to assign the respective pixels into a segmentation. For example, the training images may be prepared by overlaying the clinical image with an operator-delineated or computer-identified segmentation map. The specific architecture of network 900 in specific examples may vary based on the application (e.g., the complexity of the image data being segmented), but in some examples the network may include a number of convolution layers 912 along the contracting path and an equal number of expanding convolution layers along the up sampling path, each of which may be associated with regularization and pooling (e.g., as shown in FIGS. 10A and 10B).

Figure 11:
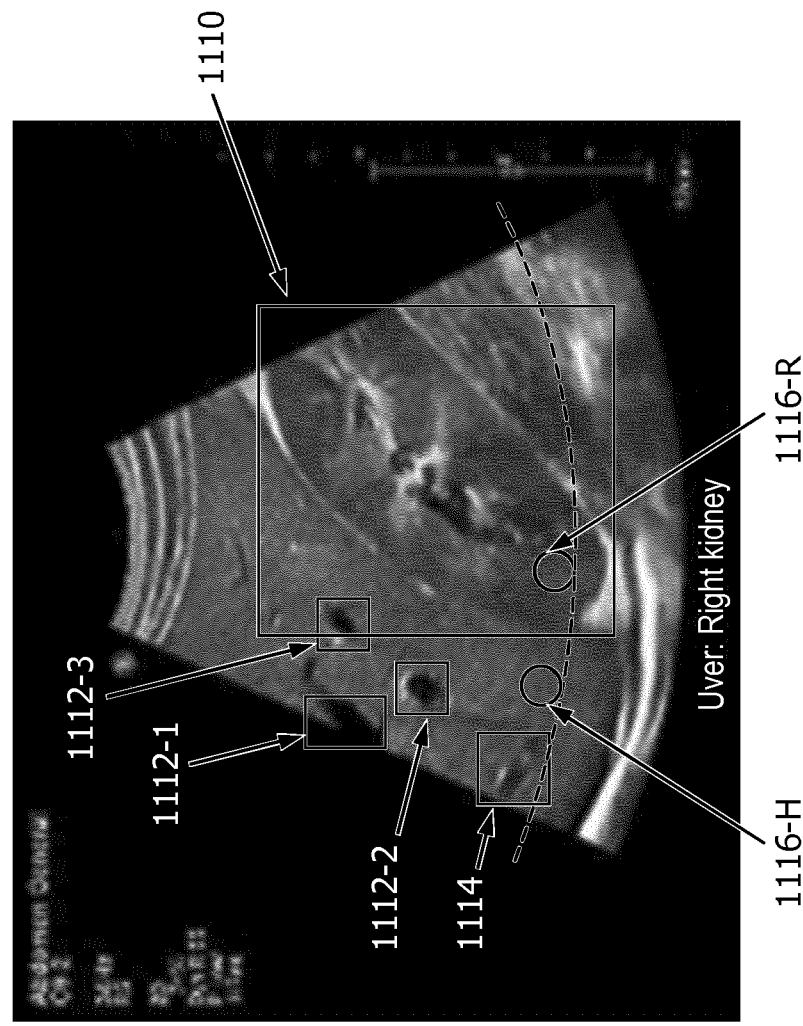
FIG. 11 shows an example of an ultrasound image with a plurality of different classes of objects detected therein in accordance with the principles of the present disclosure.

In yet further examples, the one or more networks may be trained, additionally or alternatively, to perform object detection. A number of neural network architectures have been developed for detecting objects in an image, such as the YOLO (you only look once) network, and any such object detection network may be used as a starting point (e.g., as pre-trained network) which is then fine-tuned with further training specifically on medical image data to detect clinically relevant objects within an ultrasound image. For example as shown in FIG. 11, an object detection network may be trained to recognize, in preferred examples in real-time (e.g., as each frame is received), the presence and location of any number of categories of object, for example kidney (e.g., bounding box 1110), vessel (e.g., bounding boxes 1112-1, 1112-2, and 1112-3), and other categories or classes of objects (e.g., bounding box 1114) which may be present in an image of the target anatomy. Such object detection network may output the probability of the input image containing one or more of the classes of object and their respective locations (e.g., in the form of bounding boxes around the detected object(s)). The object detection network may be operatively connected (e.g., by coupling the output of the object detection network) to one or more other networks (e.g., a classification or other type of neural network) or to a non-machine-learning post processing component to determine whether the input image corresponds the target image view and output a confidence score based on this determination.

The system may utilize the results of the segmentation or object detection to recommend ROI placement. For example, upon completion of the segmentation of the input image, the system may utilize, the segmentation map to recommend suitable locations for ROI placement, such that the recommended ROIs can be reliable used for an accurate computation of the echo-intensity ratio. Similarly, the results of the object detection process may be used to guide ROI placement. For example, having identified different classes of object and their locations/bounding boxes within the image (e.g., a region corresponding to kidney, and one or more regions corresponding to other structures such as vessels and lesions), the system can automatically identify groups of pixels in the image that meet the criteria for suitable measurement ROIs, for example, groups of pixels located at the same depth within the liver and the kidney and corresponding to generally uniform tissue (e.g., not otherwise overlapping other bodily structures, such as vessels or lesions). As shown in FIG. 11, the processor may indicate on the image one or more pairs of recommended ROIs 1116-R and 1116-H for quantification, for example by indicating a first groups of pixels with the bounding box associated with detected object of category kidney (e.g., bounding box 1110) and by indicating a second group of pixels at the same depth in the image but outside of the bounding box 1110 and not otherwise overlapping other bounding boxes associated with other structures (such as vessels, lesions etc.)

Figure 12:
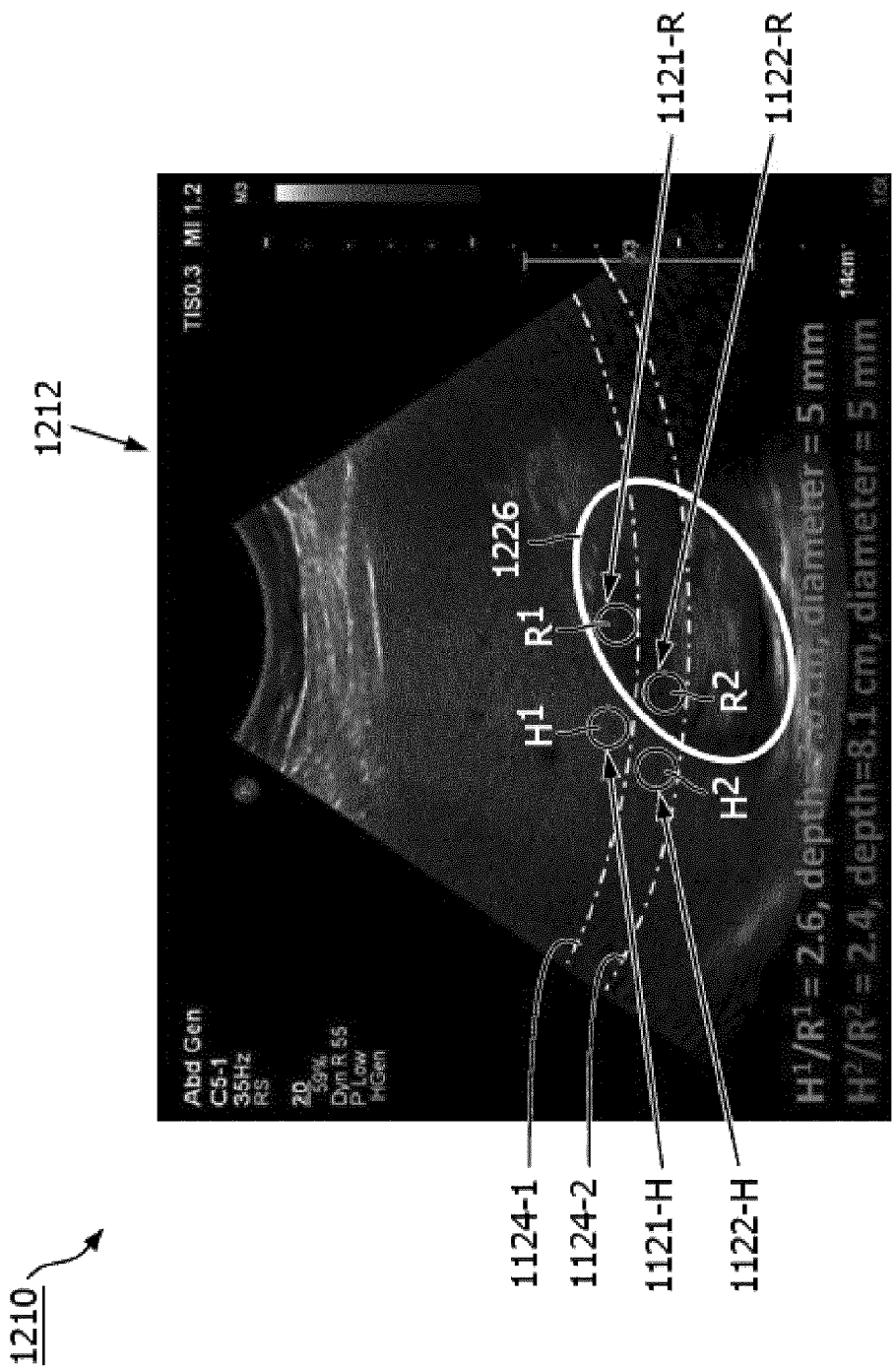
FIG. 12 shows an example ultrasound display with automated ROI placement recommendation in accordance with the principles of the present disclosure.

FIG. 12 shows an example screen capture of an ultrasound system display 1210, which shows an image 1212, which has been identified to represent a suitable view for quantification. One or more sets of recommended ROIs may now be provided by the system, e.g. by processor 223. In the illustrated example, two sets of recommended ROIs are shown on the displayed image, but it will be understood that a different number of pairs of ROIs may be recommended in other examples, e.g., only a single pair which is deemed to be at the optimal location, or multiple (2, 3, 4, or more) pairs and a ratio may be computed for each of the pairs such that statistical analysis can be used to determine the final computed echo-intensity ratio. In some examples a ratio is only computed with respect to one pair of ROIs.

In the specific example in FIG. 12, a first set of ROIs including hepatic ROI 1221-H and renal ROI 1221-R are identified, e.g., by processor 223, with circular markers located, responsive to the processor 223, on the image at a first depth. A second set of ROIs including a hepatic ROI 1222-H and renal ROI 1222-R are identified, e.g., by processor 223, with second set of circular markers located, responsive to the processor 223, at a second depth in the image. Notably, each recommended pair of ROIs is selected such that the ROIs in the pair are at the same depth, which in the case of a curved transducer corresponds to the ROIs residing along the same arc 1224-1 or 1224-2. The sets of recommended ROIs, if multiple sets are determined, may be presented to the user concurrently or in sequence, allowing the user to confirm or select the desired pair of ROIs. In some examples, the display may also include an indicator delineating the kidney tissue as determined by the segmentation step such that the user may visualize and better appreciate the placement of the recommended ROIs, and/or a depth indicator (e.g., arcs 1224-1 and 1224-2) again allowing the user to appreciate and visually confirm the proper placement of the recommended ROIs. In some embodiments, the selection of a suitable ROI may proceed without user involvement, e.g., with the system determining the optimal ROI placement. In such embodiments, the system may employ pre-programmed logic (e.g., a rules-based decision tree) or a properly trained neural network to determine the most suitable placement of the measurement ROIs, such that the selected ROIs represent substantially uniform tissue of each parenchyma (e.g., the liver and kidney), such that the ROIs do not overlap artefact-inducing structures and such that they are placed at the same depth.

Upon selection of the desired ROI pair, which may be responsive to the user input (e.g. by clicking on either one of the two ROIs in a given pair, or by clicking on the depth indicator (e.g., arc 1224-1 or 1224-2)) or responsive to automatic selection by the system, the system automatically proceed with computing the H/R echo-intensity ratio. To compute the H/R echo-intensity ration, the system divides a representative value of the echo-intensities in the first or haptic ROI by a representative value of the echo-intensities in the second or renal ROI. The representative value may be an average value of the echo-intensity values of all pixels in the ROI or some other representative value (e.g., a mean, median, or other), which may be obtained e.g., through histogramming or other statistical analysis technique. The computation of the H/R echo-intensity ratio may be performed using raw RF data (e.g., prior to log compression), which may enhance the accuracy of the quantification.

Figure 13:
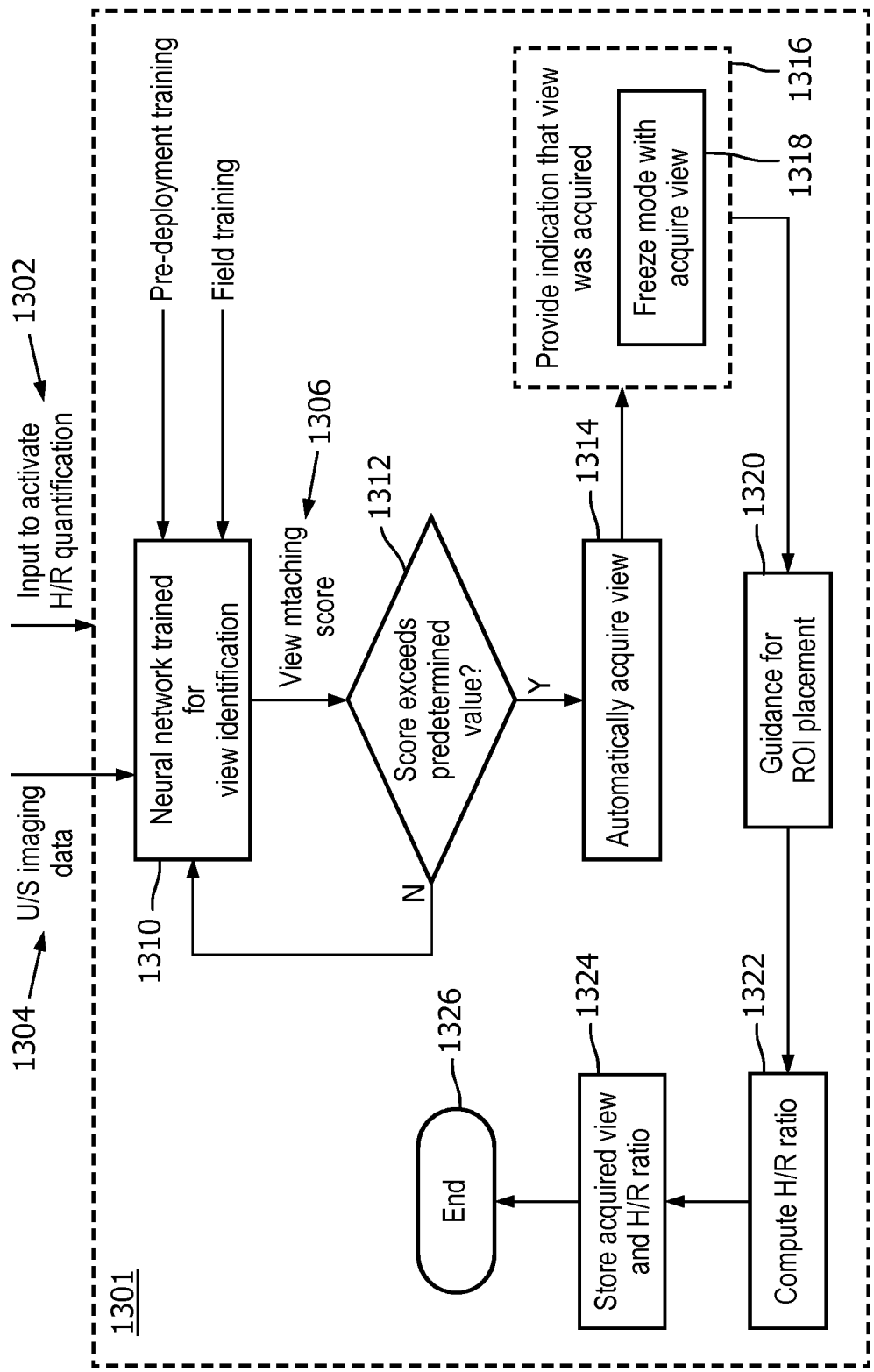
FIG. 13 is a flow diagram of a process for H/R ratio quantification in accordance with some examples of the present disclosure.

A method of ultrasonically inspecting biological tissue in accordance with some examples herein may include receiving, by a processor of an ultrasound system, a real-time ultrasound image representative of one or more types of biological tissue and providing the real-time ultrasound image to at least one convolutional neural network trained to output a confidence metric for each input image. FIG. 13 shows a flow diagram of an example process in accordance with the principles of the present disclosure. As shown in FIG. 13, the process may begin by a processor 1301 of ultrasound system receiving an ultrasound image (at block 1304) and receiving an input to activate the H/R quantification process (at bock 1302). The ultrasound image data is coupled to a neural network (block 1310) trained to identify if the image view in the incoming ultrasound image corresponds to a desired view. View matching or identification may be performed in accordance with any of the examples herein, such as by classifying the image into one of a plurality of categories which qualitatively represent the suitability of the image for quantification. The neural network at block 1310 may compute a confidence metric (e.g., a view matching score 1306). As described, the confidence metric may be indicative of a probability of the real-time ultrasound image visualizing the biological tissue in accordance with a target image view, for example in the context of liver imaging a sagittal view visualizing sufficient amount of the liver and right kidney cortex such to allow placement of measurement ROIs within substantially uniform tissue of the liver parenchyma and kidney cortex.

If the confidence metric is determine to meet a criteria (e.g., if the confidence metric is indicative of the view being a suitable view, such as by the view matching score exceeding a certain value), at block 1312, the process continues with block 1314 by the automatically capturing (storing in local memory) the image. If the confidence metric is determine not to meet the criteria, the process returns to block 1310 and the neural network receives and analyzes the next image frame. While the system is in intelligent scanning mode (e.g., during execution of the H/R quantification application, the view matching is repeated until a suitable view has been identified. The system may be configured to provide an indication that a matching view has been acquired (at block 1316), for example in the form of an audible sound being generated by the system, by the system automatically initiating freeze mode with the acquired image displayed on the display (block 1318), or a combination of the two. Other types of feedback may be provided (e.g., tactile, by a slight vibration of the probe following acquisition of the suitable view) as indication that a view has been identified.

The process then continues with providing guidance for ROI placement, as shown in block 1320. The system may be configured to determine locations of at least one pair of ROIs for example by segmenting the captured image to identify regions within the image corresponding to different types of tissue (e.g., liver and kidney). The processor may then indicate, on the displayed image, a group of pixels within the liver region as the recommended hepatic ROI and indicate another group of pixels at a same depth in the image but within the kidney cortex as the recommended renal ROI. Multiple such recommended pairs may be presented on the image. The system may await selection of one or more of the recommended pairs of ROIs and upon receiving and the selection may compute the H/R ratio for each pair of ROIs (block 1322). The computed ratio(s) may be stored with the image data (at block 1324) and the process may end (block 1326). As described herein, the image segmentation, as well as other steps of the process may be performed by one or more properly trained neural networks. The network(s) may be trained prior to deployment in a commercial system, and/or additional training may be performed in the field using subsequently acquired image data (e.g., from real patient exams, which may be automatically annotated or labeled by the system or diagnosing clinician in a manner suitable to employ then as further training data).

Although examples of producing medical images from sparsely sampled data are described herein with reference to ultrasound image data, it will be understood that the examples herein are equally applicable to training a neural network to produce images from a sparse dataset of any imaging modality, such as magnetic resonance imaging (MRI), computed tomography (CT), positron emission tomography (PET), and virtually any other imaging modality.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
a probe configured to transmit ultrasound toward a subject for generating an image of biological tissue of the subject;
a display; and
a processor configured to receive the image and to output, using at least one neural network, a confidence metric that indicates a probability of the image visualizing the biological tissue in accordance with a target image view, wherein the processor is further configured to generate a graphical indicator comprising a color bar representative of a current value of the confidence metric, and cause the graphical indicator to be displayed on the display and be dynamically updated on the display responsive to each new confidence metric output by the at least one neural network, and wherein the processor is further configured, in response to a value of the confidence metric exceeding a threshold value, to:
select the image;
segment the image to identify regions of the image associated with at least two different types of biological tissue;
determine locations of first and second regions of interest (ROIs) in the image by identifying first and second plurality of pixels, respectively, each associated with one of the at least two different types of biological tissue; and
compute a ratio of echo-intensity values of the first and second ROIs.

2. The system of claim 1, wherein the processor is further configured, if the value of the confidence metric does not exceed a threshold value, to automatically receive one or more successive real-time image frames and output a confidence metric for each of the one or more successive real-time image frames.

3. The system of claim 1, wherein the biological tissue includes at least one of hepatic tissue, renal tissue, or a combination thereof, and wherein the neural network is trained to produce a confidence metric that exceeds the threshold value if the input image corresponds to a sagittal liver and right kidney view suitable for computing a hepatic-renal echo-intensity ratio.

4. The system of claim 1, wherein the at least one neural network includes a convolutional neural network trained to segment an input image to generate a segmentation map, and wherein the confidence metric is based, at least in part, on the segmentation map of the input image.

5. The system of claim 1, wherein the at least one neural network includes a deep convolutional network trained to detect an object within an input image and to output a location of the detected object and a probability of the detected object corresponding to a target object category, and wherein the confidence metric is based on the probability.

6. The system of claim 5, wherein the processor is configured to determine the locations of first and second regions of interest (ROIs) based on the location of the detected object.

7. The system of claim 1, wherein the at least one neural network comprises a deep convolutional network configured to classify an input image into one of a plurality of classifications corresponding to a plurality of confidence metrics.

8. The system of claim 1, wherein the processor is configured to determine the locations for the first and second regions of interest by:
automatically identifying and displaying at least one pair of recommended ROIs concurrently with the image; and
receiving an indication of a selection of a pair of recommended ROIs from the at least one pair of recommended ROIs, wherein the processor is configured to set the first and second regions of interest to correspond to the selected pair of recommended ROIs.

9. The system of claim 1, wherein the color bar comprises a sliding bar wherein the sliding bar moves along the color bar responsive to each new confidence metric output by the at least one neural network.

10. A method of ultrasonically inspecting biological tissue of a subject, the method comprising:
receiving, by a processor of an ultrasound system, a real-time ultrasound image representative of one or more types of biological tissue;
providing the real-time ultrasound image to at least one convolutional neural network trained to output a confidence metric for each input image, wherein the confidence metric is indicative of a probability of the real-time ultrasound image visualizing the biological tissue in accordance with a target image view;

in response to a value of the confidence metric exceeding a threshold value:
automatically storing the real-time ultrasound image in memory of the ultrasound system;
segmenting the stored image to identify regions of the stored image associated with at least two different types of biological tissue;
determining locations of first and second regions of interest (ROIs); and
computing a ratio of an echo-intensity value of the first region of interest and an echo-intensity value of the second regions of interest (ROIs), and wherein determining the locations of the first and second ROIs includes identifying first and second plurality of pixels, respectively, each associated with one of two different types of biological tissue; and
displaying, on a display of the ultrasound system, a graphical indicator comprising a color bar comprising a sliding bar wherein the position of the sliding bar is representative of a current value of the confidence metric.

11. The method of claim 10, wherein the biological tissue represented in the real-time ultrasound image includes at least one of hepatic tissue, renal tissue, or a combination thereof, and wherein the target image view corresponds to a sagittal liver and right kidney view suitable for computing a hepatic-renal echo-intensity ratio.

12. The method of claim 10, wherein the at least one convolutional neural network is trained to segment an input image to generate a segmentation map, the method further comprising computing the confidence metric based on the segmentation map of the real-time image.

13. The method of claim 12, wherein the at least one convolutional neural network includes a fully convolutional network configured to propagate the input image along a contracting path followed by an expanding path to generate the segmentation map.

14. The method of claim 10, wherein the at least one convolutional neural network comprises a deep convolutional network trained to determine a probability of an object of one or more categories of object being present in the input image and a location of the object in the input image.

15. The method of claim 10, wherein the at least one convolutional neural network comprises a deep convolutional network configured to classify an input image into one of a plurality of classifications including a classification associated with a value that exceeds the threshold value.

16. The method of claim 10, wherein the determining locations for first and second regions of interest includes:
automatically identifying and displaying at least one pair of recommended ROIs concurrently with the stored image; and
receiving an indication of a selection of a pair of recommended ROIs from the at least one pair of recommended ROIs, wherein the first and second regions of interest are set to correspond to the selected pair of recommended ROIs.

17. The method of claim 10, further comprising receiving an indication of activation of a computer-assisted liver imaging mode, and automatically providing each incoming real-time ultrasound image to the at least one convolutional neural network until a confidence metric exceeding the threshold value is output by the at least one convolutional neural network.

18. The method of claim 17, wherein the displaying includes dynamically updating the sliding bar to represent the current value of the confidence metric as updated for each incoming real-time ultrasound image.

19. The method of claim 10, further comprising automatically transitioning from real-time imaging mode to freeze mode of the ultrasound system responsive to a determination that the confidence metric exceeds the threshold value, and wherein the transitioning includes displaying the stored ultrasound image.

20. A non-transitory computer-readable medium comprising executable instructions, which when executed cause a processor of a medical imaging system to perform the method of claim 10.

21. The system of claim 9, wherein the color bar further comprises a match indicator wherein a first end of the color bar and a first color indicate a match between the image and the target image view and a second end of the color bar and a second color indicate a no-match between the image and the target image view and wherein the sliding bar moves toward the first or the second end based on the confidence metric of the image.

22. The method of claim 10, further comprising if the confidence metric does not exceed a threshold value, automatically providing one or more successive real-time images to the at least one convolutional neural network for determining a confidence metric for each of the one or more successive real-time images.

* * * * *